US009662372B2

(12) United States Patent
Bochner et al.

(10) Patent No.: US 9,662,372 B2
(45) Date of Patent: May 30, 2017

(54) COMPOSITIONS AND METHODS TO INACTIVATE AND/OR REDUCE PRODUCTION OF MICROBIAL TOXINS

(71) Applicant: BIOLOG, INC., Hayward, CA (US)

(72) Inventors: Barry Bochner, Alameda, CA (US); Xiang-He Lei, Orinda, CA (US)

(73) Assignee: BIOLOG, Inc., Hayward, CA (US)

( * ) Notice: Subject to any disclaimer, the term of this patent is extended or adjusted under 35 U.S.C. 154(b) by 0 days.

(21) Appl. No.: 14/768,084

(22) PCT Filed: Feb. 20, 2014

(86) PCT No.: PCT/US2014/017362
§ 371 (c)(1),
(2) Date: Aug. 14, 2015

(87) PCT Pub. No.: WO2014/130655
PCT Pub. Date: Aug. 28, 2014

(65) Prior Publication Data
US 2015/0374786 A1     Dec. 31, 2015

Related U.S. Application Data

(60) Provisional application No. 61/766,844, filed on Feb. 20, 2013.

(51) Int. Cl.
| | |
|---|---|
| *A61K 38/17* | (2006.01) |
| *A61K 38/05* | (2006.01) |
| *A61K 38/06* | (2006.01) |
| *A61K 45/06* | (2006.01) |
| *A61K 9/02* | (2006.01) |
| *A61K 9/00* | (2006.01) |
| *A61K 38/02* | (2006.01) |

(52) U.S. Cl.
CPC ............ *A61K 38/17* (2013.01); *A61K 9/0019* (2013.01); *A61K 9/02* (2013.01); *A61K 38/02* (2013.01); *A61K 38/05* (2013.01); *A61K 38/06* (2013.01); *A61K 38/1703* (2013.01); *A61K 45/06* (2013.01)

(58) Field of Classification Search
None
See application file for complete search history.

(56) References Cited

U.S. PATENT DOCUMENTS

| 8,088,888 | B2 | 1/2012 | O'Neil | 530/300 |
| 2003/0149090 | A1 | 8/2003 | Gehlsen et al. | 514/400 |
| 2009/0087478 | A1 | 4/2009 | Hansen et al. | 424/450 |
| 2011/0257078 | A1 | 10/2011 | Young et al. | 514/2.7 |
| 2012/0071398 | A1 | 3/2012 | O'Neil | 514/2.6 |

OTHER PUBLICATIONS

Brown et al., Polyarginine, Polylysine and Protamine Mimic the Effects of High Extracellular Calcium Concentrations on Dispersed Bovine Parathyroid Cells, Journal of Bone and Mineral Research, 1991, 1217-1225.*
Darouiche, et al., "Efficacy of Combination of Chlorhexidine and Protamine Sulphate against Device-Associated Pathogens." *J Antimicrob Chemother*, 61(3):651-657 (2008).
Gerding and Johnson "Management of *Clostridium difficile* Infection: Thinking inside and Outside the Box." *Clin Infect Dis*, 51(11):1306-1313 (2010).
Liang, et al., "The Minimal Functional Sequence of Protamine." *Biochem Biophys Res Commun*, 336(2):653-659 (2005).
Oezguen, et al., "Clostridial Toxins: Sensing a Target in a Hostile Gut Environment." *Gut Microbes*, 3(1):35-41 (2012).
Puri, et al., "Rational Design of Inhibitors and Activity-Based Probes Targeting *Clostridium difficile* Virulence Factor Tcdb." *Chem Biol*, 17(11):1201-1211 (2010).
Teichman, et al., "Protamine Sulfate and Vancomycin Are Synergistic against *Staphylococcus* Epidermidis Prosthesis Infection in Vivo." *J Urol*, 152(1):213-216 (1994).
Yamakawa, et al., "Inhibition of Enhanced Toxin Production by *Clostridium difficile* in Biotin-Limited Conditions." *J Med Microbiol*, 47(9):767-771 (1998).
Brogden "Antimicrobial Peptides: Pore Formers or Metabolic Inhibitors in Bacteria?". *Nat Rev Microbiol*, 3(3):238-250 (2005).
David, "Towards a Rational Development of Anti-Endotoxin Agents: Novel Approaches to Sequestration of Bacterial Endotoxins with Small Molecules." *J Mol Recognit*, 14(6):370-387 (2001).
Stevens, et al., "Effect of Antibiotics on Toxin Production and Viability of *Clostridium perfringens.*" *Antimicrob Agents Chemother*, 31(2):213-218 (1987).
Wang, et al., "Apd2: The Updated Antimicrobial Peptide Database and Its Application in Peptide Design." *Nucleic Acids Res*, 37(Database issue):D933-937 (2009).
Abdeen, et al., "Peptide Inhibitors Targeting *Clostridium difficile* Toxins A and B." *ACS Chem Biol*, 5(12):1097-1103 (2010).
Bender, et al., "A Small-Molecule Antivirulence Agent for Treating *Clostridium difficile* Infection." *Sci Transl Med*, 7(306):306ra148 (2015).
Jarrad, et al., "*Clostridium difficile* Drug Pipeline: Challenges in Discovery and Development of New Agents." *J Med Chem*, 58(13):5164-5185 (2015).
Tam, et al., "Small Molecule Inhibitors of *Clostridium difficile* Toxin B-Induced Cellular Damage." *Chem Biol*, 22(2):175-185 (2015).
Valdes, et al., "Monitoring in Real Time the Cytotoxic Effect of *Clostridium difficile* Upon the Intestinal Epithelial Cell Line Ht29." *J Microbiol Methods*, 119:66-73 (2015).

* cited by examiner

*Primary Examiner* — Lianko Garyu
(74) *Attorney, Agent, or Firm* — Medlen & Carroll, LLP

(57) ABSTRACT

The present invention is related to compositions and methods to treat, ameliorate and/or prevent morbidity and/or mortality from microbial infections. In particular, bacterial infections that are associated with the production and release of bacterial toxins. For example, many Clostridia bacteria, such as *Clostridium difficile*, release toxins resulting in tissue and organ damage and death, even after antibiotic therapy that either reduces or eliminates the bacteria. In particular, various peptides, polypeptides, and proteins are disclosed herein that either inactivate *Clostridium difficile* toxin and/or reduce *Clostridium difficile* toxin production.

10 Claims, 23 Drawing Sheets

FIGURE 1

| | | | | | | | |
|---|---|---|---|---|---|---|---|
| Protamine #1 | PRRRR* | SSSRP* | IRRRR* | PRRAS* | RRRRR* | RGGRR* RR | SEQ ID NO: 1 |
| I-1 | | | RRRR* | PRRAS* | | | SEQ ID NO: 2 |
| I-2 | PRRRR* | SSSRP* | I | | | | SEQ ID NO: 3 |
| III-1 | PRRRR* | SSSRP* | IRRRR* | PRRAS* | RR | | SEQ ID NO: 4 |
| II-1 | | | | | RRRRR* | RGGRR* RR | SEQ ID NO: 5 |
| II-5 | | RP* | IRRRR* | PRRAS* | RRRRR* | RGG | SEQ ID NO: 6 |
| I-1 | PRRRR* | SSSRP* | | | | | SEQ ID NO: 7 |
| | | | | | | | |
| Protamine #2 | PRRRR* | SSSRP* | VRRRR* | PRRVS* | RRRRR* | RGGRR* RR | SEQ ID NO: 8 |
| II-3 | | | VRRRR* | PRRVS* | RRRRR* | RGG | SEQ ID NO: 9 |
| III-2 | | | RRRR* | PRRVS* | RRRRR* | RGGRR* RR | SEQ ID NO: 10 |
| II-1 | | | | | RRRRR* | RGGRR* RR | SEQ ID NO: 11 |
| II-2 | RRRR* | SSSRP* | VRRRR | | | | SEQ ID NO: 12 |
| I-1 | PRRRR* | SSSRP* | | | | | SEQ ID NO: 13 |
| | | | | | | | |
| Protamine #3 | PRRRR* | SSRRP* | VRRRR* | PRRVS* | RRRRR* | RGGRR* RR | SEQ ID NO: 14 |
| II-3 | | | VRRRR* | PRRVS* | RRRRR* | RGG | SEQ ID NO: 15 |
| III-2 | | | RRRR* | PRRVS* | RRRRR* | RGGRR* RR | SEQ ID NO: 16 |
| II-1 | | | | | RRRRR* | RGGRR* RR | SEQ ID NO: 17 |
| II-1 | | | | | RRRRR* | RGGRR* RR | SEQ ID NO: 18 |
| I-2 | | | RRRR* | PRRV | | | SEQ ID NO: 19 |
| | | | | | | | |
| Protamine #4 | PRRRR* | ASRRI* | RRRRR* | PRVSR* | RRRRG* | CRRRR* | SEQ ID NO: 20 |
| II-4 | PRRRR* | ASRRI* | RRRRR* | PRV | | | SEQ ID NO: 21 |
| I-2 | | I* | RRRRR* | PR | | | SEQ ID NO: 22 |

C. *diff* toxin B (ng/ml)

Protamine sulfate (ug/ml)

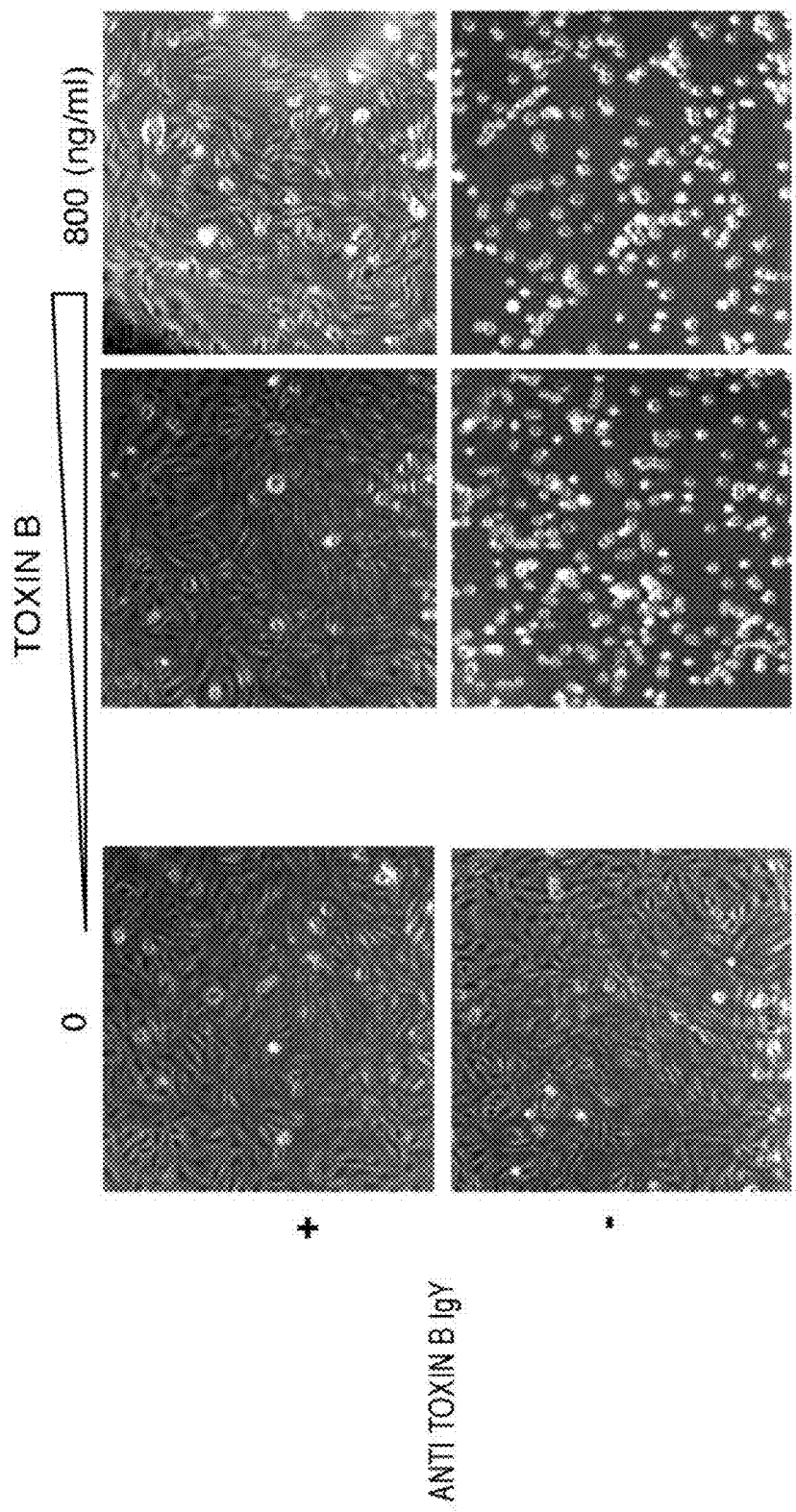

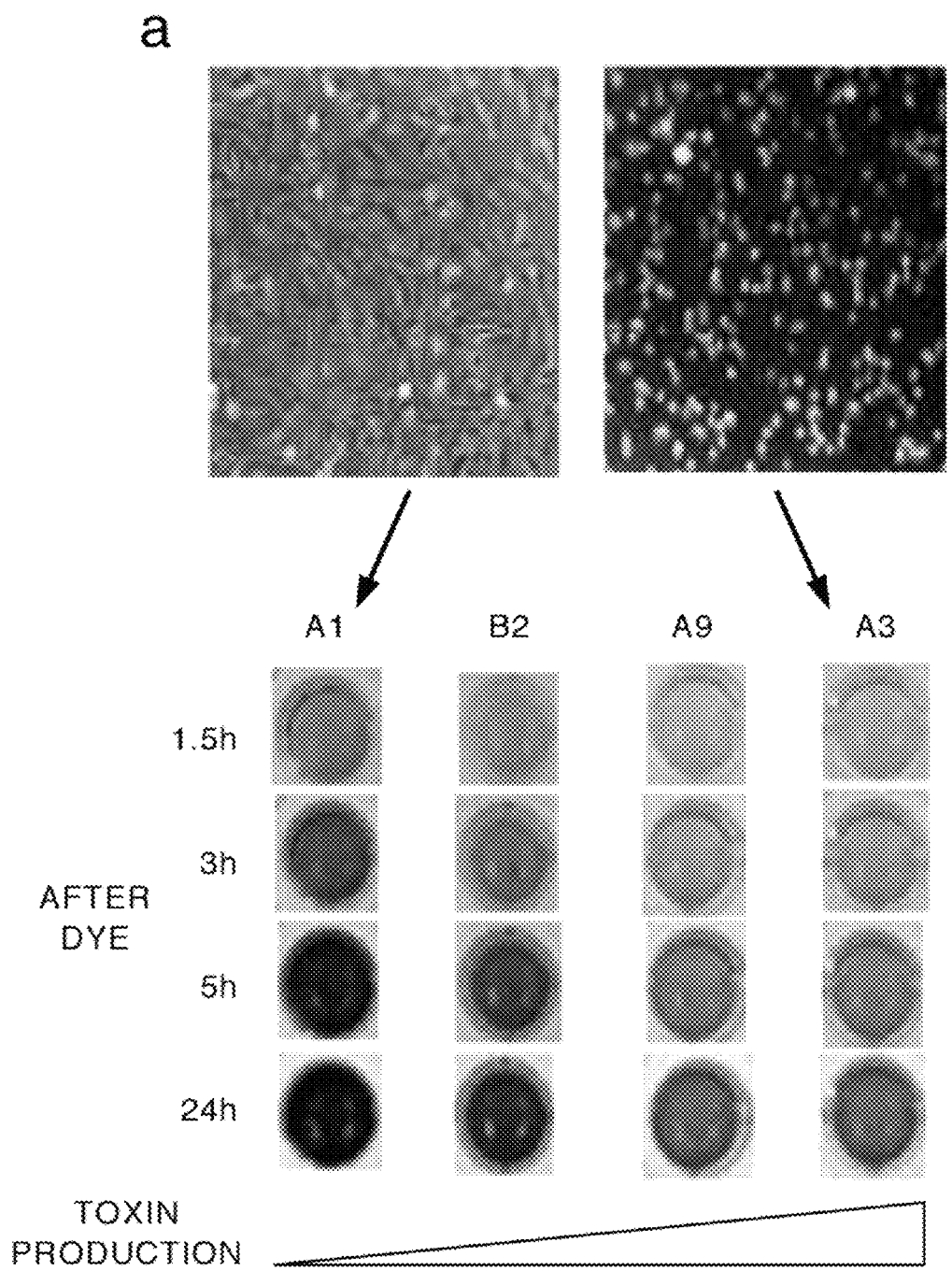
FIG. 11A-a

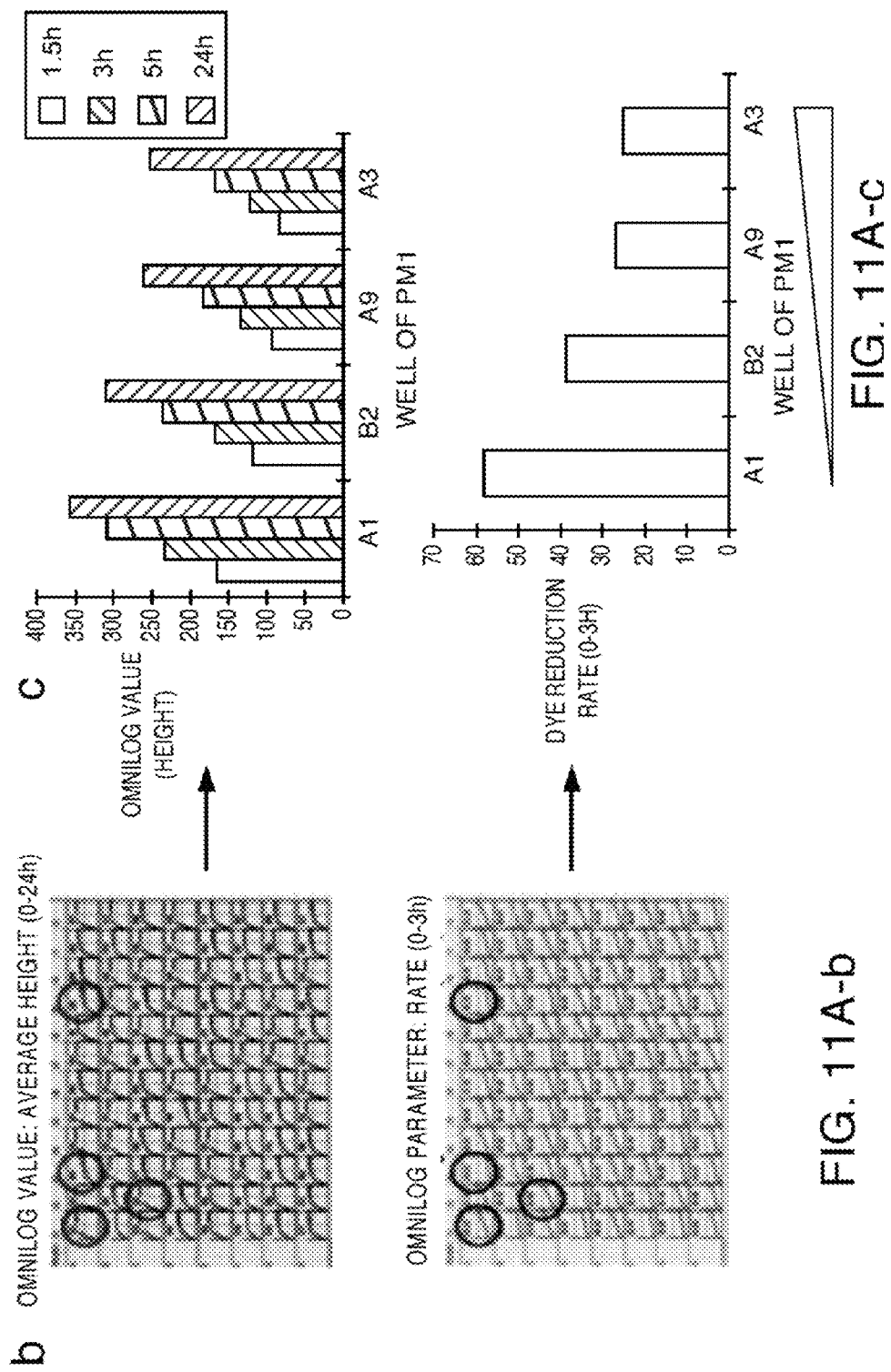
FIG. 11A-b
FIG. 11A-c

FIG. 13A

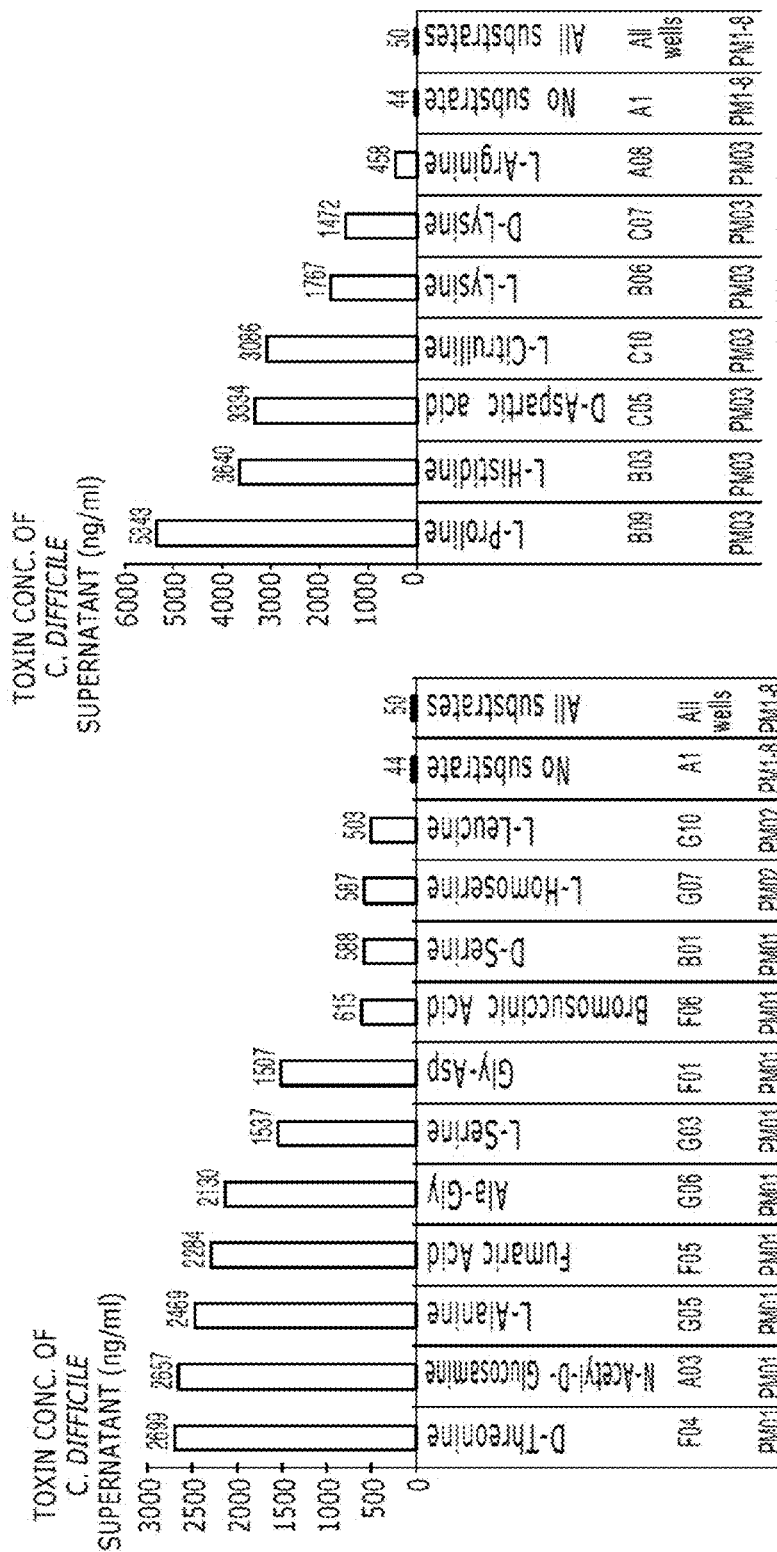

Grow *C. difficile* on BUA+B plates

↓

Inoculate bacterial cells into Biolog PM panels

↓

Incubate *C. difficile* in anaerocic chamber at 36°C for 3 days

↓

Collect bacterial toxin-containing supernatants after filtration

↓

Expose mammalian cells (e.g., CHO-k1) to *C. difficile* toxins

⟶

Incubate the mammalian cells with toxins in $CO_2$ incubator at 37°C for 18-20 hours

↑

Observe and record morphological changes of the cells microscopically

↑

Add reducible dye to the cells and collect dye reduction data automatically and kinetically using OmniLog instrument

↑

Analyze data using specialized software and acquire quantitative and informative information about bacterial toxin production under certain conditions

Figure 16

COMPOSITIONS AND METHODS TO INACTIVATE AND/OR REDUCE PRODUCTION OF MICROBIAL TOXINS

FIELD OF THE INVENTION

The present invention is related to compositions and methods to treat, ameliorate and/or prevent morbidity and/or mortality from microbial infections. In particular, bacterial infections that are associated with the production and release of bacterial toxins. For example, many Clostridia bacteria, such as *Clostridium difficile*, release toxins resulting in tissue and organ damage and death, even after antibiotic therapy that either reduces or eliminates the bacteria. In particular, various peptides, polypeptides, and proteins are disclosed herein that either inactivate *Clostridium difficile* toxin and/or reduce *Clostridium difficile* toxin production.

BACKGROUND

The current global outbreak of *Clostridium difficile* infection exemplifies the major public health threat posed by clostridial toxins. In the western world, *C. difficile* infection is one of the most prolific causes of bacterial-induced diarrhea and potentially fatal colitis. Two pathogenic enterotoxins, Toxin A and Toxin B, cause the disease. Vancomycin and metronidazole remain readily available treatment options for treating *C. difficile* infection, but neither is fully effective as is evident by high clinical relapse and fatality rates. Thus, there is an urgent need to find an alternative therapy that preferentially targets the toxins and not the pathogen. Oezguen et al., "Clostridial toxins: Sensing a target in a hostile gut environment" *Gut Microbes* 3:135-41 (2012). This application describes novel potential therapies.

The dramatic increase in severity of *C. difficile*-associated disease in North America and Europe over the last decade highlights the clinical prominence of *C. difficile*'s glucosylating toxins, and is partially due to the spread of new epidemic-associated strains, for example BI/NAP1/027 that produce high amounts of these toxins. Accompanying this surge in disease severity is a rise in recurrent clinical episodes in up to 35% of patients (CDI). DuPont H.L., "The search for effective treatment of *Clostridium difficile* infection" *N Engl J Med* 364:473-475 (2011). These unmet clinical issues represent a significant medical and financial challenge to health care systems, and have rekindled interest in improving therapy against this increasingly prevalent pathogen. Oezguen et al., "Clostridial toxins: Sensing a target in a hostile gut environment" *Gut Microbes* 3:135-41 (2012).

What is needed in the art, and what are described in this application, are safe and effective therapeutic compounds that can effectively inactivate microbial toxins, either systemically or within the localized area of infection. Another beneficial therapeutic approach described in this invention is the use of novel chemical agents that can inhibit toxin production.

SUMMARY OF THE INVENTION

The present invention is related to compositions and methods to treat, ameliorate and/or prevent morbidity and/or mortality from microbial infections. In particular, bacterial infections that are associated with the production and systemic release of bacterial toxins. For example, many Clostridia bacteria, such as *Clostridium difficile*, release systemic toxins resulting in tissue and organ damage and death, even after antibiotic therapy that either reduces or eliminates the bacteria. In particular, various peptides, polypeptides, and proteins are disclosed herein that either inactivate *Clostridium difficile* toxin and/or reduce *Clostridium difficile* toxin production.

In one embodiment, the present invention contemplates a method, comprising: a) providing; i) a patient comprising a bacterial toxin; ii) a therapeutic cationic protein; b) administering said therapeutic protein to said patient; and c) inactivating said bacterial toxin with said bacterial toxin. In one embodiment, the therapeutic cationic protein is selected from at least one of the group consisting of protamine, protamine III-2 peptide, polyarginine and polylysine. In one embodiment, the bacterial toxin has spread systemically. In one embodiment, the bacterial toxin is primarily localized to the colon. In one embodiment, the bacterial toxin is a Clostridia toxin. In one embodiment, the Clostridia toxin is a *C. difficile* Toxin A or B. In one embodiment, the inactivating comprises a specific binding between said bacterial toxin and said cationic protein. In one embodiment, the inactivating comprising a non-specific binding between said bacterial toxin and said cationic protein. In one, embodiment, the method further comprises administering an antibiotic before step (b). In one embodiment, the method further comprises administering an antibiotic along with step (b). In one embodiment, the method further comprises administering a chemical agent that suppresses toxin production along with step (b).

In one embodiment, the present invention contemplates a method, comprising: a) providing; i) a patient exhibiting at least one symptom of a microbial infection; ii) a composition comprising a cationic polypeptide selected from at least one of the group including, but not limited to, protamine and/or protamine III-2 peptide; b) administering said composition to said patient under conditions such that said at least one symptom is reduced. In one embodiment, the bacterial infection is a Clostridia infection. In one embodiment, the Clostridia infection is a *C. difficile* infection. In one embodiment, the composition is formulated into a pharmaceutical composition. In one embodiment, the method further comprises administering an antibiotic before step (b). In one embodiment, the method further comprises administering a toxin production inhibitor before step (b).

In one embodiment, the present invention contemplates a method, comprising: a) providing; i) a patient comprising a bacteria, wherein the bacteria is producing a toxin; ii) a leucine peptide; b) administering said leucine peptide to said patient; and c) reducing said bacterial toxin production with said leucine peptide. In one embodiment, the leucine peptide is selected from at least one of the group consisting of a leucine dipeptide and a leucine tripeptide. In one embodiment, the bacteria is a Clostridia bacteria. In one embodiment, the Clostridia bacteria is a *C. difficile* bacteria. In one embodiment, the toxin is a *C. difficile* Toxin B. In one embodiment, the toxin is a *C. difficile* Toxin A. In one embodiment, the method further comprises administering a polycationic polypeptide.

In one embodiment, the present invention contemplates a method, comprising: a) providing; i) a patient exhibiting at least one symptom of a bacterial infection; ii) a leucine peptide; b) administering said leucine peptide to said patient under conditions such that said at least one symptom is reduced. In one embodiment, the bacterial infection is a Clostridia infection. In one embodiment, the Clostridia infection is a *C. difficile* infection. In one embodiment, the leucine peptide is formulated into a pharmaceutical composition. In one embodiment, the leucine peptide is a dipeptide.

In one embodiment, the leucine peptide is a tripeptide. In one embodiment, the method further comprises administering a polycationic polypeptide.

DEFINITIONS

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc) to a binding partner under conditions such that the binding partner becomes unresponsive to its natural ligands Inhibitory compounds may include, but are not limited to, small organic molecules, antibodies, and proteins/peptides.

The term "pulmonary injury" as used herein, refers to any effect on pulmonary tissue that impairs it functional or structural integrity. For example, injury may be a result of, but not limited to, inhalation of toxins, surgical procedures, or accident.

The term "injury" as used herein, denotes a bodily disruption of the normal integrity of tissue structures. In one sense, the term is intended to encompass surgery. In another sense, the term is intended to encompass irritation, inflammation, infection, and the development of fibrosis. In another sense, the term is intended to encompass wounds including, but not limited to, contused wounds, incised wounds, lacerated wounds, non-penetrating wounds (i.e., wounds in which there is no disruption of the skin but there is injury to underlying structures), open wounds, penetrating wound, perforating wounds, puncture wounds, septic wounds, subcutaneous wounds, burn injuries etc.

The term "fibroblast migration" as used herein, refers to any movement of a fibroblast in the direction of tissue injury. Such migration is usually stimulated by chemotactic factors (i.e., for example, lysophosphatidic acid) released by white blood cells.

The term "vascular leak" as used herein, refers to an increase in vascular permeability due to tissue injury. Such a condition may result in internal bleeding and blood coagulation, inflammation, and ultimately the development of fibrosis.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "medium" as used herein, refers to any material, or combination of materials, which serve as a carrier or vehicle for delivering of a drug to a treatment point (e.g., wound, surgical site etc.). For all practical purposes, therefore, the term "medium" is considered synonymous with the term "carrier". It should be recognized by those having skill in the art that a medium comprises a carrier, wherein said carrier is attached to a drug or drug and said medium facilitates delivery of said carrier to a treatment point. Further, a carrier may comprise an attached drug wherein said carrier facilitates delivery of said drug to a treatment point. Preferably, a medium is selected from the group including, but not limited to, foams, gels (including, but not limited to, hydrogels), xerogels, microparticles (i.e., microspheres, liposomes, microcapsules etc.), bioadhesives, or liquids. Specifically contemplated by the present invention is a medium comprising combinations of microparticles with hydrogels, bioadhesives, foams or liquids. Preferably, hydrogels, bioadhesives and foams comprise any one, or a combination of, polymers contemplated herein. Any medium contemplated by this invention may comprise a controlled release formulation. For example, in some cases a medium constitutes a drug delivery system that provides a controlled and sustained release of drugs over a period of time lasting approximately from 1 day to 6 months.

The term "drug" or "compound" as used herein, refers to any pharmacologically active substance capable of being administered that achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, enema, suppository etc.

The term "patient", as used herein, is a human or animal and need not be hospitalized. For example, outpatients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "test compound" as used herein, refers to any compound or molecule considered a candidate as an inhibitory compound.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are often obtained by partial hydrolysis of proteins. In general, a peptide comprises amino acid polymers having an order of magnitude of two to fifty amino acids.

The term "polypeptide" as used herein, refers to any of various amides that are derived from two or more amino acids by combination of the amino group of one acid with the carboxyl group of another and are often obtained by partial hydrolysis of proteins. A used herein, the term polypeptide is used to include the entire range, from the size of peptides to the size of proteins.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to "apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "biocompatible", as used herein, refers to any material does not illicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The term "biodegradable" as used herein, refers to any material that can be acted upon biochemically by living cells or organisms, or processes thereof, including water, and broken down into lower molecular weight products such that the molecular structure has been altered.

The term "bioerodible" as used herein, refers to any material that is mechanically worn away from a surface to which it is attached without generating any long-term inflammatory effects such that the molecular structure has not been altered. In one sense, bioerosin represents the final stages of "biodegradation" wherein stable low molecular weight products undergo a final dissolution.

The term "bioresorbable" as used herein, refers to any material that is assimilated into or across bodily tissues. The bioresorption process may utilize both biodegradation and/or bioerosin.

The term "biostable" as used herein, refers to any material that remains within a physiological environment for an intended duration resulting in a medically beneficial effect.

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

A "variant" of a protein is defined as an amino acid sequence that differs by one or more amino acids from a polypeptide sequence or any homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide is defined as a novel nucleotide sequence that differs from a reference oligonucleotide by having deletions, insertions and substitutions. These may be detected using a variety of methods (e.g., sequencing, hybridization assays etc.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring *Bacillus anthracis* BclA.

A "substitution" results from the replacement of one or more nucleotides or amino acids by different nucleotides or amino acids, respectively.

The term "derivative" as used herein, refers to any chemical modification of a nucleic acid or an amino acid. Illustrative of such modifications would be replacement of hydrogen by an alkyl, acyl, or amino group. For example, a nucleic acid derivative would encode a polypeptide that retains essential biological characteristics.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells that lack protein activity with an expression vector which expresses the protein, a derivative thereof, or a portion thereof.

The terms "arrays" and "microarrays" are used somewhat interchangeably differing only in general size. The instant invention involves the same methods for making and using either. Each array typically contains many cells (typically 100 1,000,000+) wherein each cell is at a known location and contains a specific component of interest. Each array therefore contains numerous different components of interest.

In a related aspect, "device" is used to describe both arrays and microarrays, where the array or microarray may comprise other defined components including surfaces and points of contact between reagents.

BRIEF DESCRIPTION OF THE FIGURES

FIG. 1 presents the cationic amino acid clusters in the four protamine subunits. The conservative sequence of four protamine components is highlighted in the box.

FIG. 2 shows a representative experiment using a ninety-six (96) microwell array with Biolog Dye Mix MB showing cell viability as demonstrated by dye reduction color changes.

FIG. 5 presents exemplary data showing that the protamine III-2 peptide inactivates *Clostridium difficile* Toxin B-mediated metabolic poisoning as measured by dye reduction assay. X-axis: actual (prepared) toxin B at 100 ng/ml, 33.3 ng/ml, 11.1 ng/ml, 3.7 ng/ml and 1.2 ng/ml; Y-axis: measured toxin B by dye reduction rate. Large Squares: Positive Control. Diamonds: Toxin B+0.09 μM protamine III-2 peptide. Small Squares: Toxin B+0.26 μM protamine III-2 peptide. Triangle: Toxin B+0.77 μM protamine III-2 peptide. Crosses: Toxin B+2.31 μM protamine III-2 peptide. Hatched Crosses: Toxin B+6.94 μM protamine III-2 peptide. Circle: Toxin B+20.8 μM protamine III-2 peptide. Half Square: Toxin B+62.5 μM protamine III-2 peptide.

FIG. 8 presents the exemplary data of FIG. 4 replotted on a logarithmic scale.

Figure 13A:
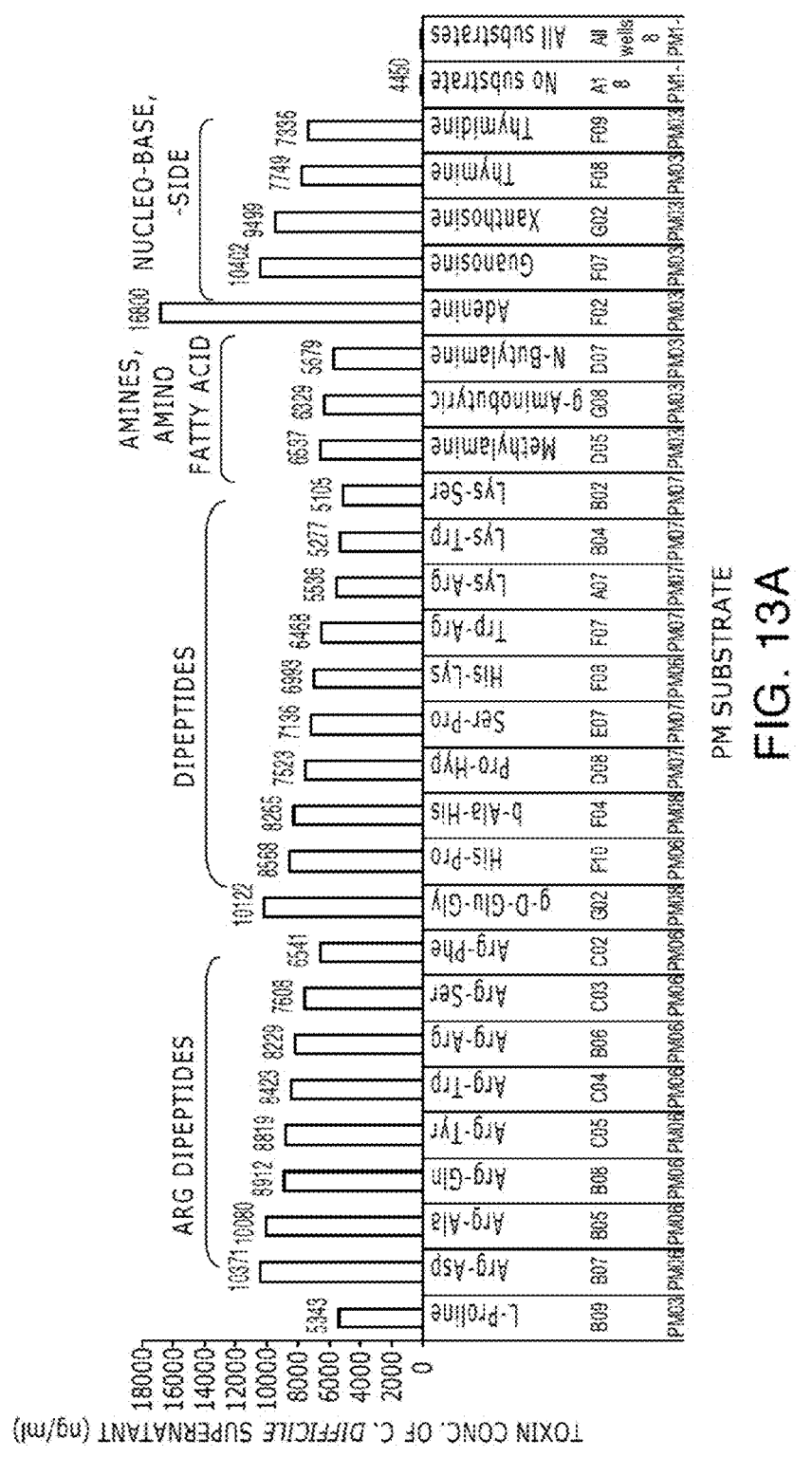

FIG. 13 presents exemplary data of high toxin-inducing PM substrates for C. difficile ATCC 9689. A. Top toxin inducers. Note that adenine as a nitrogen source is the strongest toxin inducer of all tested PM substrates in this study. g-D-Glu-Gly=γ-D-Glu-Gly; b-Ala-His=β-Ala-His; g-Aminobutyric=γ-Aminobutyric acid. B. High toxin production induced by some carbon sources in PM1 and 2. C. High toxin production induced by some amino acids as nitrogen sources. Note that L-proline is the highest toxin inducer in the amino acid category.

Figure 3:
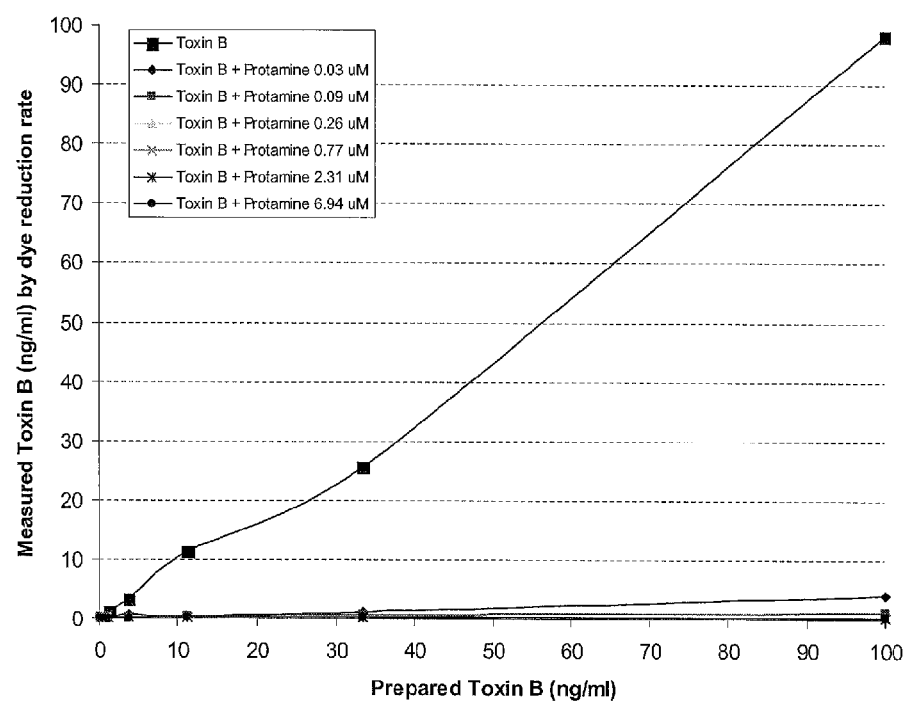
FIG. 3 presents exemplary data showing that the protamine protein inactivates *Clostridium difficile* Toxin B-mediated metabolic poisoning as measured by the dye reduction assay. X-axis: actual (prepared) toxin B at 100 ng/ml, 33.3 ng/ml, 11.1 ng/ml, 3.7 ng/ml and 1.2 ng/ml; Y-axis: measured toxin B by dye reduction rate. Large Squares: Positive Control. Diamonds: Toxin B+0.03 μM protamine. Small Squares: Toxin B+0.09 μM protamine. Triangle: Toxin B+0.26 μM protamine. Crosses: Toxin B+0.77 μM protamine. Hatched Crosses: Toxin B+2.31 μM protamine. Circle: Toxin B+6.94 μM protamine.

A. Cytotoxin assay comparison of Clostridial species. Five µl of bacterial supernatant from each well of the PM of each Clostridial species, C. difficile (ATCC 9689), C. perfringens (ATCC 25763), and C. sordellii (ATCC 9714), were used in this assay. CHO-k1 is the indicator cell in this dye reduction assay. Upper panel: supernatants from PM1; Lower panel: supernatants from PM6. In the lower panel, the wells above the lines contain arginine dipeptides as the nitrogen source.

B. Aerobic bacterial toxin assays and comparison of supernatants from PM1 between toxigenic and non toxigenic strains or species. Vero is the indicator cell for E. coli strains and Shigella species. CHO-k1 is the indicator cell for Listeria species. Upper panel: toxigenic strains or species; Lower panel: non-toxigenic strains or species.

FIG. 16 presents an illustrative flow chart of the process used in this study to quantitate toxin production by C. difficile under hundreds of culture conditions using PM technology.

DETAILED DESCRIPTION OF THE INVENTION

The present invention is related to compositions and methods to treat, ameliorate and/or prevent morbidity and/or mortality from microbial infections. In particular, bacterial infections that are associated with the production and release of bacterial toxins. For example, many Clostridia bacteria, such as Clostridium difficile, release toxins resulting in tissue and organ damage and death, even after antibiotic therapy that either reduces or eliminates the bacteria. In particular, various peptides, polypeptides, and proteins are disclosed herein that either inactivate Clostridium difficile toxin and/or reduce Clostridium difficile toxin production.

The data presented herein show the effects of various compounds that may inactivate Clostridium difficile toxin. For example, compounds having a high cationic surface charge may be useful to mediate this effect (e.g., for example, protamine, protamine III-2, polyarginine and/or polylysine). In one embodiment, these cationic proteins can provide a useful treatment against *Clostridium difficile* toxin when administered parenterally or via other routes. Although it is not necessary to understand the mechanism of an invention, it is believed that bacterial toxin inactivation may be mediated by a direct interaction between the cationic protein and the toxin, thereby eliminating the toxin's biological effects.

The data presented herein also show the effects of various compounds that may reduce the production of *Clostridium difficile* toxin. For example, peptides predominantly containing the amino acid L-leucine, including, but not limited to, leucine dipeptides and/or leucine tripeptides. Although it is not necessary to understand the mechanism of an invention, it is believed that reduction of bacterial toxin production may be mediated by the effect of L-leucine on the CodY regulatory gene.

I. *Clostridium difficile* Infection

In one embodiment, the present invention contemplates a method for treating a bacterial infection by administering a cationic protein, either before or after or during, antibiotic therapy. In one embodiment, the cationic protein binds to a bacterial toxin thereby inactivating the toxin. Although it is not necessary to understand the mechanism of an invention, it is believed that the presently contemplated methods are effective in reducing and/or eliminating tissue/organ damage caused by residual bacterial toxin, either before, or after killing the bacteria.

In 1978, *Clostridium difficile*, a Gram-positive, spore-forming anaerobic *bacillus*, was identified as a gastrointestinal pathogen that frequently causes diarrhea and more seriously pseudomembranous colitis in patients undergoing antibiotic treatment. George et al., "Aetiology of antimicrobial-agent-associated colitis" Lancet 1:802-803 (1978); Aronsson et al., "Occurrence of toxin-producing *Clostridium difficile* in antibiotic-associated diarrhea in Sweden" Med Microbiol Immunol 170:27-35 (1981); Bartlett et al., "Role of *Clostridium difficile* in antibiotic-associated pseudomembranous colitis" Gastroenterology 75:778-782 (1978). Besides diarrhea, the symptoms of *C. difficile* infection (CDI) include, but are not limited to, abdominal pain, fever, loss of appetite, nausea, toxic megacolon, perforations of the colon and/or sepsis.

Most importantly, death also can result from the toxin(s). With the emergence of hypervirulent strains, the mortality rate of CDI has risen dramatically. Among serious cases, 15,000-20,000 patients die annually from CDI in the United States. Rupnik et al., *Clostridium difficile* infection: new developments in epidemiology and pathogenesis" Nat Rev Microbiol 7:526-536 (2009). *C. difficile* is also an animal pathogen. Songer et al., "*Clostridium difficile*: an important pathogen of food animals" Anaerobe 12 1-4 (2006).

During the past decade, the prevalence and severity of CDI has increased dramatically worldwide. The emerging epidemic of "hypervirulent" isolates represented by ribotype 027 (also called BI/NAP1/027), which are variant strains of toxinotype III, have been identified as a pathogenic source in hospital or hospital associated CDI outbreaks. Comparative genomic analyses showed that the epidemic 027 strains have gained 234 additional genes during the past two decades, which may account for their epidemic proficiency and their higher case-fatality ratio. He et al., "Evolutionary dynamics of *Clostridium difficile* over short and long time scales" Proc Natl Acad Sci USA 107:7527-7532 (2010); Stabler et al., "Comparative phylogenomics of *Clostridium difficile* reveals clade specificity and microevolution of hypervirulent strains" J Bacteriol 188: 7297-7305 (2006); Stabler et al., "Comparative genome and phenotypic analysis of *Clostridium difficile* 027 strains provides insight into the evolution of a hypervirulent bacterium" Genome Biol 10: R102 (2009); Stabler et al., "In-depth genetic analysis of *Clostridium difficile* PCR-ribotype 027 strains reveals high genome fluidity including point mutations and inversions" Gut Microbes 1:269-276 (2010); Sebaihia et al., "The multi drug-resistant human pathogen *Clostridium difficile* has a highly mobile, mosaic genome" Nat Genet 38:779-786 (2006); Warny et al., "Toxin production by an emerging strain of *Clostridium difficile* associated with outbreaks of severe disease in North America and Europe" Lancet 366: 1079-1084 (2005); McDonald et al., "An epidemic, toxin gene-variant strain of *Clostridium difficile*" N Engl J Med 353:2433-2441 (2005); Tae et al., "The first case of antibiotic-associated colitis by *Clostridium difficile* PCR ribotype 027 in Korea" J Korean Med Sci 24:520-524 (2009); Lim et al., "Isolation of the first three cases of *Clostridium difficile* polymerase chain reaction ribotype 027 in Singapore" Singapore Med J 52: 361-364 (2011); Loo et al., "A predominantly clonal multi-institutional outbreak of *Clostridium difficile*-associated diarrhea with high morbidity and mortality" N Engl J Med 353: 2442-2449 (2005).

The pathogenesis of *C. difficile* involves virulence factors, for example, Toxin A and Toxin B. Although it is not necessary to understand the mechanism of an invention, it is believed that the cause-effect relationship between the toxins and the pathological changes they engender in animal cells, and cytopathic effects (CPE), have been shown to be due to inactivation of Rho-GTPase through glucosylation by the toxins. Just et al., "Glucosylation of Rho proteins by *Clostridium difficile* toxin B" Nature 375: 500-503 (1995); Gerhard et al., Glucosylation of Rho GTPases by *Clostridium difficile* toxin A triggers apoptosis in intestinal epithelial cells" J Med Microbiol 57: 765-770 (2008); Just et al., *Clostridium difficile* toxin B acts on the GTP-binding protein Rho" J Biol Chem 269: 10706-10712 (1994); Just et al., "The enterotoxin from *Clostridium difficile* (ToxA) monoglucosylates the Rho proteins" J Biol Chem 270: 13932-13936 (1995).

The roles the toxins play in *C. difficile* pathogenesis have also been demonstrated in multiple animal models and in clinical settings. Kuehne et al., "The role of toxin A and toxin B in *Clostridium difficile* infection" Nature 467: 711-713 (2010); Czuprynski et al., "Pseudomembranous colitis in *Clostridium difficile*-monoassociated rats" Infect Immun 39: 1368-1376 (1983); Chang et al., "Clindamycin-induced enterocolitis in hamsters as a model of pseudomembranous colitis in patients" Infect Immun 20: 526-529 (1978); Knoop F. C., "Clindamycin-associated enterocolitis in guinea pigs: evidence for a bacterial toxin" Infect Immun 23: 31-33 (1979); Lyerly et al., "Effects of *Clostridium difficile* toxins given intragastrically to animals" Infect Immun 47: 349-352 (1985); Bongaerts et al., "Role of toxins A and B in the pathogenesis of *Clostridium difficile* disease" Microb Pathog 17: 1-12 (1994); Kyne et al., "Asymptomatic carriage of *Clostridium difficile* and serum levels of IgG antibody against toxin A" N Engl J Med 342: 390-397 (2000); and Leav et al., "Serum anti-toxin B antibody correlates with protection from recurrent *Clostridium difficile* infection (CDI)" Vaccine 28: 965-969 (2010).

The quality and quantity of the toxins are directly or indirectly determined or regulated by multiple factors including, but not limited to, genetic, environmental, nutritional, and/or metabolic status. Therefore, monitoring functional toxin production is fundamental in studies of pathogenesis and epidemiology as well as in clinical diagnosis and treatment of CDI.

II. *Clostridium difficile* Toxins

Both *Clostridium difficile* Toxin A and Toxin B cause cell death through an orchestrated sequence of events Jank et al., "Structure and mode of action of clostridial glucosylating toxins: the ABCD model" *Trends Microbiol*. 16:222-229 ((2008). These multidomain toxin proteins first enter cells by triggering receptor-mediated endocytosis. Frisch et al., "The complete receptor-binding domain of *Clostridium difficile* toxin A is required for endocytosis" *Biochem. Biophys. Res. Commun*. 300:706-711 (2003); and Rolfe et al., "Purification of a functional receptor for *Clostridium difficile* toxin A from intestinal brush border membranes of infant hamsters" *Clin. Infect. Dis*. 16 (Suppl 4):S219-S227 ((1993)).

Acidification of toxin-containing endosomal compartments subsequently initiates translocation of the N-terminal cytotoxic glucosyltransferase domain and presumably the cysteine protease domain (CPD) into the cytosol. Just et al., "Glucosylation of Rho proteins by *Clostridium difficile* toxin B" *Nature* 375:500-503 9 (1995); Pfeifer et al., "Cellular uptake of *Clostridium difficile* toxin B. Translocation of the N-terminal catalytic domain into the cytosol of eukaryotic cells" *J. Biol. Chem*. 278:44535-44541 (2003); and Qa'Dan et al., "pH-induced conformational changes in *Clostridium difficile* toxin B" *Infect. Immun*. 68:2470-2474 (2000). The CPD is activated by the eukaryotic-specific small molecule inositol hexakisphosphate (InsP6). Egerer et al., "Autocatalytic cleavage of *Clostridium difficile* toxins A and B depends on cysteine protease activity" *J. Biol. Chem*. 282: 25314-25321 ((2007); and Reineke et al., "Autocatalytic cleavage of *Clostridium difficile* toxin B" *Nature* 446:415-419 (2007). This activation catalyzes the autoproteolytic release of the toxin's cytotoxic glucosyltransferase domain from the endosomal membrane. The liberated effector domain then monoglucosylates small Rho family GTPases, resulting in loss of cell-cell junctions and ultimately cell death. Gerhard et al., "Glucosylation of Rho GTPases by *Clostridium difficile* toxin A triggers apoptosis in intestinal epithelial cells" *J. Med. Microbiol*. 57:765-770 ((2008); and Qa'Dan et al., "*Clostridium difficile* toxin B activates dual caspase-dependent and caspase-independent apoptosis in intoxicated cells" *Cell. Microbiol*. 4:425-434 (2002).

A majority of the *C. difficile* bacterial strains that cause disease in humans secrete two large toxins, Toxin A (308 kDa) and Toxin B (270 kDa). There is little ambiguity that these pathogenic toxins are the major cause of CDI since toxin-deficient clinical isolates are avirulent and may form a new line of clinical therapy by competing with pathogenic strains. Microbial genetic manipulation studies have highlighted the disease-inducing potential of both toxins but implicate Toxin B as the primary virulence factor in CDI, supporting earlier unequivocal reports that Toxin B is the major enterotoxin in the human colon. Lyras et al., "Toxin B is essential for virulence of *Clostridium difficile*" *Nature* 458:1176-1179 (2009); Kuehne et al, "The role of toxin A and toxin B in *Clostridium difficile* infection" *Nature*; 467: 711-713 (2010); Savidge et al., "*Clostridium difficile* toxin B is an inflammatory enterotoxin in human intestine" *Gastroenerology* 125:413-420 (2003); and Reigler et al., "*Clostridium difficile* toxin B is more potent than toxin A in damaging human colonic epithelium in vitro" *J. Clin Invest*. 95:2004-2011 (1995).

III. Current Antimicrobial Treatment of *Clostridium difficile* Infections

Antimicrobials have been the agents of choice for treatment of *Clostridium difficile* infection (CDI) for 130 years, primarily metronidazole and vancomycin. Antimicrobials have been highly successful and are likely to continue to play a major role in the treatment of patients who already have CDI. However, there remain several areas of CDI treatment that are suboptimal—namely, the management of fulminant or complicated severe CDI and management of recurrent CDI.

Patients with fulminant disease frequently experience failure to respond to medical management with antimicrobials and either die or require subtotal colectomy as a life-saving measure. Antimicrobial treatment is thought to be, at least in part, responsible for frequent CDI recurrences, presumably as a result of the unintended effects on the normal gastrointestinal microbiota that leave patients vulnerable to relapse or reinfection. As a result, a number of non-antimicrobial management approaches have been proposed and under development, some of which have entered clinical trials. In addition, new antimicrobial treatments designed to improve response and to avoid damage to the microbiota are also under clinical development. Gerding et al., "Management of *Clostridium difficile* Infection: Thinking Inside and Outside the Box" *Healthcare Epidemiology* 51:1306-1313 (2010).

Shortly after the infectious cause of pseudomembranous colitis was recognized, oral vancomycin and metronidazole were demonstrated as effective treatments, although vancomycin is the only agent that has received US Food and Drug Administration (FDA) approval for this indication. Early prospective, randomized trials concluded that metronidazole was not inferior to vancomycin. Recurrent infections, however, occurred at substantial rates for both agents, and avoiding this complication remains a major unmet need in CDI management. Gerding et al. (supra).

The Gram-positive anaerobic bacterium *Clostridium difficile* is a cause of hospital-acquired diarrhea and severe gastrointestinal illness pseudomembranous colitis. Kelly et al., "*Clostridium difficile*—more difficult than ever" *N Engl. J. Med*. 359:1932-1940 (2008); and Rupnik et al., "*Clostridium difficile* infection: new developments in epidemiology and pathogenesis" *Nat. Rev. Microbiol*. 7:526-536 ((2009). Although infection rates have risen dramatically in the last decade, there is currently a lack of therapeutics to treat *C. difficile* infection. Halsey, J. "Current and future treatment modalities for *Clostridium difficile*-associated disease" *Am. J. Health Syst. Pharm*. 65:705-715 ((2008). This is in large part due to the organism's resistance to most classes of antibiotics.

IV. Antimicrobial Effects of Cationic Polypeptides

Homopolymers or peptides containing a high percentage of cationic amino acids have been shown to have a unique ability to cross the plasma membrane of cells, and consequently have been used to facilitate the uptake of a variety of biopolymers and small molecules. Polymers of L- or D-arginine containing six or more amino acids have been reported to enter cells far more effectively than polymers of equal length composed of lysine, ornithine and histidine. Peptides of fewer than six amino acids were ineffective. The length of the arginine side-chain may be varied without significant loss of activity. These data, combined with the inability of polymers of citrulline to enter cells, demonstrated that the guanidine headgroup of arginine played a structural role for the biological activity. Cellular uptake could be inhibited by preincubation of the cells with sodium azide, but not by low temperature (3° C.), indicating that the process was energy dependent, but did not involve endocytosis. Mitchell et al., "Polyarginine enters cells more efficiently than other polycationic homopolymers" *J Pept Res.* 56(5):318-325 (2000).

Protamine and polyarginine are reported to have bacteriolytic effects indicating that their primary sites of action are cell wall or membrane components. For example, *Bacillus subtilis* requires a high polycation multiplicity per cell for cell lysis, displaying multi-hit lysing kinetics; the bacteriolysis was inhibited by trypsin, pronase, purified polyanionic wall polysaccharide, and by dissociative actions of salt hypemolarities used in isolation of nucleic acids. The inactivation of polycation lytic abilities during bacteriolysis was accompanied by modifications in electrophoretic migration of protamine and polyarginine. It was suggested as a mechanism of cell lysis that the multiple zonal surface condensations of polyanionic wall components by basic polypeptides may be similar to chromatin DNA picnosis. Antohi et al., "Protamine and polyarginine bacteriolysis. Similarities in its mechanism with chromatin DNA picnosis" *Z Naturforsch C.* 34(12):1144-1150 (1979).

It has been reported that peptides comprising cationic amino acids can be used in the treatment of microbial infections (e.g., $(X)_i(Y)_m)_n$), wherein 1, m and n are integers from 0 to 10, and X and Y can be either hydrophobic or cationic amino acids. This peptide formula encompasses peptides ranging from 2 amino acids to 200 amino acids in length. These peptides are suggested to be useful in the treatment of microbial infections. In particular, polylysine and/or polyarginine were shown to inhibit fungal infections such as *T. interdigitale, T. rubrum* and/or *Candida albicans*. Although no data was presented, these peptides were further suggested to be useful against various bacterial species including Clostridia, *Staphylococcus, Enterococcus* etc. O'Neil D., "Method Of Treatment Of A Fungal Infection With Poly Arginine Peptides" U.S. Pat. No. 8,088,888; O'Neil D., "Anti-Microbial Peptides" United States Patent Application Publication Number 2012/0071398 (both herein incorporated by reference). Nonetheless, a direct interaction between a cationic amino acid/peptide and a systemic bacterial toxin was not addressed and no in vivo data was represented.

The cationic compound, histamine, and histamine derivatives, may be effective in treating a variety of bacterial-related infections. Although it is not necessary to understand the mechanism, it is believed that that histamine acts to inhibit reactive oxygen metabolites that are believed to mediate some injurious effects of bacterial infections. This is unlike the action of the presently contemplated polycationic proteins that are believed to directly bind to systemic bacterial toxins Gehlsen et al., "Compositions For The Treatment Of Infectious Diseases" United States Patent Application Publication Number 2003/0149090 (herein incorporated by reference).

Imidazole may have an enhanced antibacterial effect on *Clostridium difficile* when combined with the polycationic antibacterial, polymyxin B. Although it is not necessary to understand the mechanism, it is believed that polymyxin B acts on the surface of the bacteria to disrupt the membrane. This is unlike the action of the presently contemplated polycationic proteins that are believed to directly bind to systemic bacterial toxins. Young et al., "Antibacterial Combination Therapy For The Treatment Of Gram Positive Bacterial Infections" United States Patent Application Publication Number 2011/0257078 (herein incorporated by reference).

Protamine sulfate was previously reported as an effective in vitro bactericidal against *Staphylococcus epidermidis*, but it is suggested that the mechanism of action of protamine sulfate involves binding to the bacterial surface and disrupting the protective layer of the biofilm. This is unlike the action of the presently contemplated polycationic proteins that are believed to directly bind to systemic bacterial toxins. Further, the in vivo data showed that protamine sulfate, alone, failed to have any effect on *S. epidermidis* infection. Teichman et al., "Protamine Sulfate And Vancomycin Are Synergistic Against *Staphylococcus Epidermidis* Prosthesis Infection In Vivo: *J Urol.* 152:213-216 (1994).

A combination of protamine sulfate and chlorhexidine had significant anti-microbial effects against *E. coli, Pseudomonas aeruginosa* and *Staphylococcus epidermidis* when tested in vitro. However, the effects of protamine sulfate when given alone had little or no effect. Darouiche et al., "Efficacy of combination of chlorhexidine and protamine sulphate against device-associated pathogens" *Journal of Antimicrobial Chemotherapy* 61:651-657 (2008).

Contrary to the substantial literature cited above documenting the ability of cationic polypeptides to kill microorganisms, we can find no evidence of any prior discovery of the ability of cationic polypeptides to inactivate microbial toxins. This is the novel invention that we have made and are herein disclosing.

V. Bacterial Toxin Inactivation by Cationic Polypeptides

In one embodiment, the present invention contemplates a novel non-antimicrobial approach to counteracting microbial toxins. Existing non-antimicrobial approaches to CDI treatment and prevention can be divided into 3 groups: intraluminal toxin binders or neutralizers, biotherapeutics to restore the protective microbiota, and antibodies (active and passive) to improve CDI immunity.

Toxin-binding agents, such as the anion-exchange resins cholestyramine and colestipol, were initially thought to be beneficial in CDI management, but a placebo-controlled clinical trial of colestipol showed no advantage over placebo, and in the hamster model, cholestyramine also proved ineffective. Mogg et al., "Randomized controlled trial of colestipol in antibiotic-associated colitis" *Br J Surg* 69:137-139 (1982); and Kurtz et al., "GT160-246, a toxin binding polymer for treatment of *Clostridium difficile* colitis" *Antimicrob Agents Chemother* 45:2340-2347 (2001).

Toxin binding has also been attempted with antibodies to toxins A and B generated by vaccination of animals, harvesting of antibodies from milk or eggs, and oral administration of antibodies to treat or prevent CDI by neutralization of toxins in the gut lumen. Immunization of cows and chickens with toxin A and toxin B proteins has yielded antibodies in milk and eggs that, when administered orally to hamsters, protected against CDI. Bovine derived immunoglobulin G (IgG) has been found to be degraded by acid conditions and by transit through the human gastrointestinal tract; however, toxin-neutralizing activity was detectable in human feces and ileal fluid. Successful human prevention and treatment trials of bovine- and chicken-derived IgG antibodies have not been reported, possibly because of difficulty in delivering an effective neutralizing dose of IgG to the colon. Kink et al., "Antibodies to recombinant *Clostridium difficile* toxins A and B are an effective treatment and prevent relapse of *C. difficile*-associated disease in a hamster model of infection" *Infect Immun* 66:2018-2025 (1998); Lyerly et al., "Passive immunization of hamsters against disease caused by *Clostridium difficile* by use of bovine immunoglobulin G concentrate" *Infect Immun* 59:2215-2218 (1991). Kelly et al., "Anti-*Clostridium dif-*

*ficile* bovine immunoglobulin concentrate inhibits cytotoxicity and enterotoxicity of *C. difficile* toxins" *Antimicrob Agents Chemother* 40:373-379 (1996); Kelly et al., "Survival of anti-*Clostridium difficile* bovine immunoglobulin concentrate in the human gastrointestinal tract" *Antimicrob Agents Chemother* 41:236-241 (1997); Warny et al., "Bovine immunoglobulin concentrate-*Clostridium difficile* retains *C. difficile* toxin neutralising activity after passage through the human stomach and small intestine" *Gut* 44:212-217 (1999); van Dissel et al., "Bovine antibodyenriched whey to aid in the prevention of a relapse of *Clostridium difficile*-associated diarrhea: preclinical and preliminary clinical data" *J Med Microbiol* 54:197-205 (2005); Bauer et al., "Alternative strategies for *Clostridium difficile* infection" *Int J Antimicrob Agents* 33(Suppl 1):S51-S56 (2009); Mattila et al., "A randomized, double-blind study comparing *Clostridium difficile* immune whey and metronidazole for recurrent *Clostridium difficile*-associated diarrhea: efficacy and safety data of a prematurely interrupted trial" *Scand J Infect Dis* 40:702-708 (2008); and. Numan et al., "*Clostridium difficile*-associated diarrhea: bovine anti-*Clostridium difficile* whey protein to help aid the prevention of relapses" *Gut* 56:888-889 (2007).

The only currently available antibody treatment for CDI is pooled intravenous immunoglobulin (IVIG), for which only retrospective clinical evaluation for treatment of severe and recurrent CDI has been published. WIG was initially reported as effective for immunoglobulin-deficient children with chronic recurrent CDI. Leung et al., "Treatment with intravenously administered gamma globulin of chronic relapsing colitis induced by *Clostridium difficile* toxin" *J Pediatr* 118:633-637 (1991). IVIG preparations contain neutralizing levels of IgG antibody to toxin A and toxin B. Salcedo et al., "Intravenous immunoglobulin therapy for severe *Clostridium difficile* colitis" *Gut* 41:366-370 (1997). No conclusive evidence of benefit for IVIG has been demonstrated in retrospective analyses of its use for treatment of recurrent CDI, nor has an effective dose been established (range, 125-400 mg/kg in single or repeated doses). Wilcox M. H., "Descriptive study of intravenous immunoglobulin for the treatment of recurrent *Clostridium difficile* diarrhea" *J Antimicrob Chemother* 53:882-884 (2004): McPherson et al., "Intravenous immunoglobulin for the treatment of severe, refractory, and recurrent *Clostridium difficile* diarrhea" *Dis Colon Rectum* 49:640-645 (2006). For severe or fulminant CDI, one retrospective study compared 18 patients who received IVIG (dose range, 200-300 mg/kg) with a group of patients with similarly severe CDI who did not receive IVIG and found no difference in mortality, colectomy rate, or length of stay; the conclusion was that the use of IVIG for severe CDI is unsubstantiated. Juang et al., "Clinical outcomes of intravenous immune globulin in severe *Clostridium difficile*-associated diarrhea" *Am J Infect Control* 35:131-137 (2007). A larger and more recent uncontrolled, retrospective series of 21 patients with severe CDI treated with widely varying doses of IVIG demonstrated survival in only 43% of patients. Abougergi et al., "Intravenous immunoglobulin for the treatment of severe *Clostridium difficile* colitis: an observational study and review of the literature" *J Hosp Med* 5:E1-E9 (2010). Thus, to date, there are insufficient data to support use of IVIG for either recurrent or severe CDI. O'Horo et al., "The role of immunoglobulin for the treatment of *Clostridium difficile* infection: a systematic review" *Int J Infect Dis* 13:663-667 (2009).

Covalent small molecule inhibitors of *Clostridium difficile* Toxin B have been identified that inactivate Toxin B holotoxin function in cells and resolved the structure of inhibitor-bound protease to 2.0 A°. This structure reveals the molecular basis of CPD substrate recognition and informed the synthesis of activity-based probes for this enzyme. Puri et al., "Rational Design of Inhibitors and Activity-Based Probes Targeting *Clostridium difficile* Virulence Factor TcdB" *Chemistry & Biology* 17:1201-1211 (2010).

A viable strategy for combating *C. difficile* and other prominent bacterial pathogens is to target virulence factors instead of essential enzymes. Clatworthy et al., "Targeting virulence: a new paradigm for antimicrobial therapy" *Nat. Chem. Biol.* 3:541-548 ((2007); and Puri et al., "Using small molecules to dissect mechanisms of microbial pathogenesis" *ACS Chem. Biol.* 4: 603-616 (2009). This method limits the selective pressure on the organism to develop a resistance to treatment, extending the effective lifespan of the drug. The large glucosylating toxins Toxin A and Toxin B are potential targets for this approach because they may be virulence factors of *C. difficile*. Genth et al., "*Clostridium difficile* toxins: more than mere inhibitors of Rho proteins" *Int. J. Biochem. Cell Biol.* 40:592-597 ((2008); and Jank et al., "Structure and mode of action of clostridial glucosylating toxins: the ABCD model" *Trends Microbial.* 16:222-229 ((2008).). Toxin B, in particular, has been shown to be critical for virulence and is found in all clinical isolates. Lyras et al., "Toxin B is essential for virulence of *Clostridium difficile*" *Nature* 458:1176-1179 (2009).

It has been reported that *Clostridium difficile* Toxin B is a druggable target. However, inhibition of its protease active site was difficult because the small molecule is competing with an intramolecular autoproteolytic event. The most potent compound reported was a 499 Da-capped dipeptide inhibitor Hpa-SL-AOMK. In addition, a minimal interaction between the protease and inhibitor peptide backbone suggested that inhibitors with non-peptidic scaffolds can be developed to bypass the pharmacokinetic shortfalls of peptidic compounds. Puri et al., "Rational Design of Inhibitors and Activity-Based Probes Targeting *Clostridium difficile* Virulence Factor TcdB" *Chemistry & Biology* 17:1201-1211 (2010). In spite of all the approaches taken as cited above, there remains a need for a more effective treatment for CDI.

In one embodiment, the present invention contemplates a method of inactivating bacterial toxin. In one embodiment, the method further comprises preventing and/or ameliorating bacterial toxin-induced tissue and/or organ injury. In one embodiment, the method is performed either simultaneous with, or after, the administration of conventional antibiotic compounds. Bacterial toxins are known to interact with tissues and organs in such a manner that results in inflammation and/or necrosis. Although it is not necessary to understand the mechanism of the invention, it is believed that the methods disclosed herein block, as quickly as possible, the toxicity engendered by microbial toxins.

VI. Novel Technology for Measuring Microbial Toxin Production Phenotype MicroArray Technology The compounds discovered herein were screened using Phenotype MicroArray (PM) technology providing high throughput testing of culture conditions and chemical effectors. The method can quantitatively measure toxin production by microbes (e.g., for example, *C. difficile* type strain ATCC 9689) under a variety of different culture conditions (i.e., for example, 768 culture conditions). The different culture conditions include, but are not limited to, different carbon, nitrogen, phosphorus, and sulfur sources.

Phenotype MicroArrays (PM) technology provides a simple tool for testing microbial cells, as well as mammalian cells, under hundreds or thousands of culture conditions.

Bochner B. R., "New technologies to assess genotype-phenotype relationships" *Nat Rev Genet* 4:309-314 (2003); Bochner B. R. et al., "Phenotype microarrays for high-throughput phenotypic testing and assay of gene function" *Genome Res* 11:1246-1255 (2001); Bochner B. R., "Global phenotypic characterization of bacteria" *FEMS Microbiol Rev* 33:191-205 (2009); and Bochner et al., "Assay of the multiple energy-producing pathways of mammalian cells" *PLoS One* 6:e18147 (2011). It has been reported that PM's were used to examine the effect of many culture condition variables on toxin production by the pathogenic fungus, *Fusarium graminearum*. Gardiner et al., "Nutrient profiling reveals potent inducers of trichothecene biosynthesis in *Fusarium graminearum*" *Fungal Genet Biol* 46: 604-613 (2009). This fungus may be a major pathogen on wheat, with severe agricultural and commercial impact. Even after many decades of study, no one was able to find in vitro culture conditions that would turn on synthesis of the *F. graminearum* trichothecene mycotoxin. However, a breakthrough was provided by using PM technology, demonstrating that strong toxin induction could be obtained in vitro by simply culturing the fungus with arginine, putrescine, agmatine, or guanine as the nitrogen source. Secondarily, pH 4.5 was identified to produce additional induction. Gardiner et al., "Low pH regulates the production of deoxynivalenol by *Fusarium graminearum*" *Microbiology* 155: 3149-3156 (2009).

Substrate utilization effects on fungal secondary metabolite production was studied using a different approach. Singh M. P., "Application of Biolog FF MicroPlate for substrate utilization and metabolite profiling of closely related fungi" *J Microbiol Methods* 77:102-108 (2009). Ninety-five (95) substrates were combined with a scaled-down LC-MS to quantitatively profile the secondary metabolites directly from the microwell culture supernatants. These data can be useful for both characterization and optimization of secondary metabolite production by fungi.

Cell-based cytotoxicity assay (CCTA) is traditionally regarded as the gold standard assay for *C. difficile* cytotoxin and serves as the reference for other toxin assay methods. Planche et al., "Reference assays for *Clostridium difficile* infection: one or two gold standards? *J Clin Pathol* 64: 1-5 (2011). CCTA assay looks for toxin-induced CPE by microscopic detection of a shift from normal to "rounded" morphology using a toxin-sensitive adherent mammalian cell line (an indicator cell, e.g., CHO, Vero, HT-29, foreskin or others) and then verifies that the CPE is prevented by a specific toxin-neutralizing antibody. This gold standard assay is believed to be a true test for functional cytotoxin regardless of whether the DNA coding sequence of the toxin or the sequences of regulatory proteins are mutated.

Development of *C. difficile* Toxin Assays in 96-well Format.

Commercially available purified, lyophilized, *C. difficile* toxins A and B were dissolved into buffer solutions. Upon storage, it was observed that their potencies decrease rapidly with noticeable loss by the next day, even if the solutions are stored at 4° C. Consequently, standard titration curves were used from freshly dissolved purified toxins. It was also observed that the cytotoxic potency of the supernatants collected from the PM panels also decreased over time. Therefore, the assays of the toxins produced by *C. difficile* strains in PM panels (96-well format) were always carried out with fresh preparations of the supernatants, usually on the same day of collection.

Purified standard *C. difficile* toxin B (Listlab) was used to optimize and calibrate two comparative assays. A morophological assay and a colorimetric assay.

In a morphological assay, the commercial toxin caused cytopathic effects (CPE), seen microscopically as cell rounding changes, in both CHO-k1 and Vero cells. The observed CPE was active in a concentration-dependent manner. The lower panel of FIG. 10A shows an example of a toxin B titration with CHO-k1 cells. Purified toxin A (Listlab) was much less potent than toxin B against both cell lines (data not shown).

A colorimetric assay using Biolog redox dye MB and an OmniLog instrument was used to quantitatively measure the degree of intoxication of CHO-k1 and Vero cells by the toxin. In this assay also, toxin B-treated cells showed concentration-dependent intoxication of cells that resulted in decreasing rates of color formation as the killed cells were incapable of dye reduction and the dying or injured cells were compromised in the reduction (lower panel of FIG. 10B, FIG. 10C, Example V).

Figure 10B:
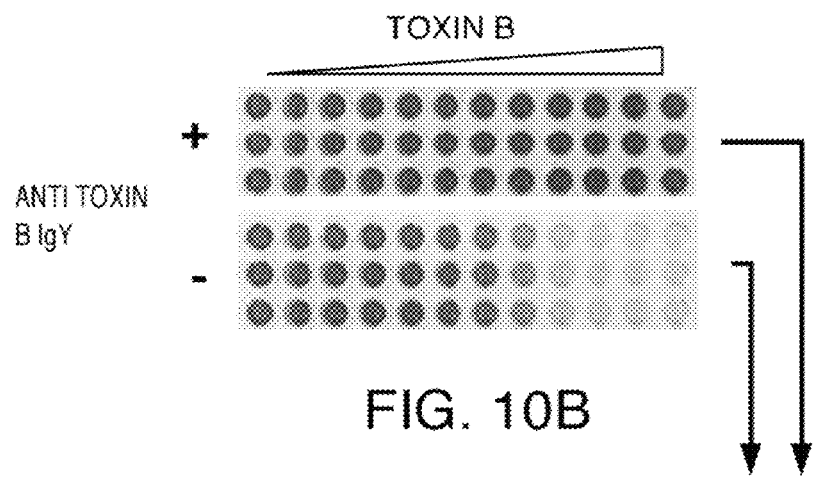
FIG. 10 presents exemplary data of cytotoxicity and neutralization assay of purified C. difficile toxin B with CHO-k1 cell line. Serial 3-fold titrations of standard toxin B (ng/ml) in the presence or absence of 2.5 µg/ml neutralizing antibodies IgY specific for toxin B. (A) CHO-k1 cell morphology changed to rounded shapes by toxin B in a dose dependent manner (the lower panel). This was prevented by the neutralizing antibodies (upper panel). (B) CHO-k1 cell dye reduction was reduced by toxin B also in a dose dependent manner (the lower panel), which corresponds to the cell morphological changes. This effect was also prevented by the neutralizing antibodies (the upper panel). (C) Quantification of the dye reduction changes by toxin B, with (Red) or without (Dark blue) 2.5 µg/ml neutralizing antibodies IgY. Light blue: toxin B with control antibodies IgY-010; Purple: no toxin B with no antibodies; Green: no toxin B with control antibodies IgY-010.
Figure 10C:
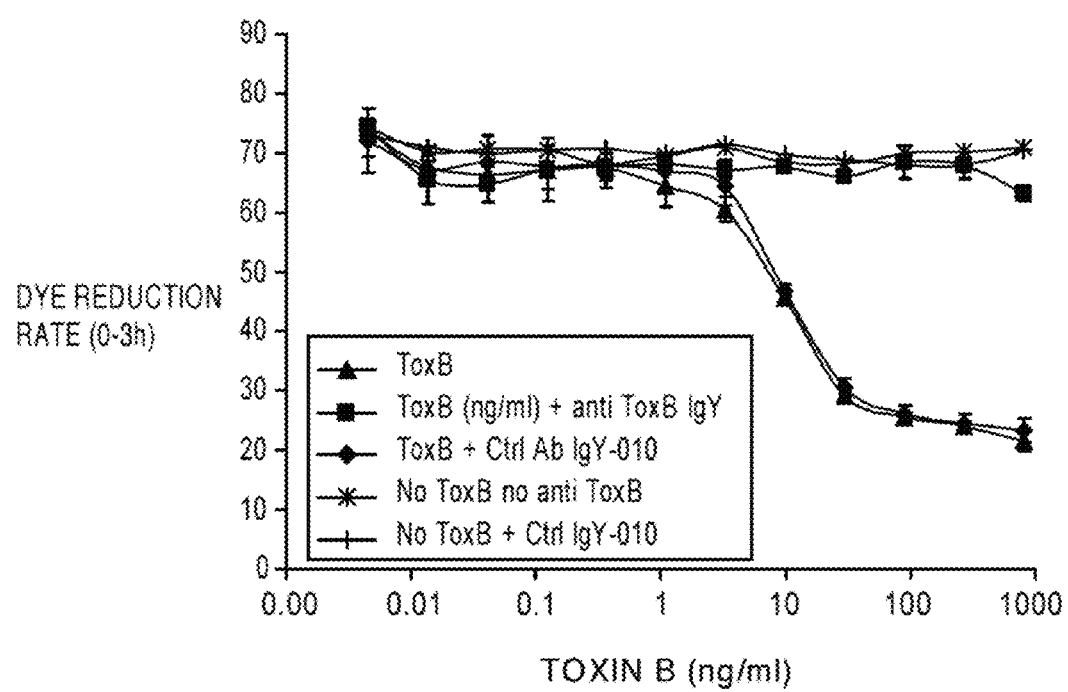

In comparison, increased cell rounding in the morphological assay was correlated with a decreased dye reduction rate in the colorimetric assay (FIGS. 10A, 10B, 10C). Neutralization of toxin B with anti-toxin B polyclonal antibodies IgY (Gallus Immunotech) provided complete protection of the indicator cells in both assays (FIGS. 10A, 10B, 10C).

The colorimetric dye reduction provided a quantitative assay of toxin over a >3 log concentration range. From serial titrations of standard toxin B, the dye reduction rates by mammalian cells were calculated using PM Analysis Software. Regression analysis on known (prepared) concentrations of toxin B and corresponding dye reduction rates by CHO-k1 cells could be accurately fit to several regression equations over a range of serial titrations of toxin B, from 800 ng/ml (~2963 pM) down to approximately 0.122 ng/ml (~0.45 pM). The predicted toxin concentrations calculated from the regression equations were very close to the prepared concentrations. See, Table 1.

TABLE 1

Predicted concentrations of *C. difficile* toxin compared to the true concentrations in cell culture assay medium

| Prepared toxin Conc. (ng/ml)[a] | Dye Reduction Rate (x)[b] | Regression Equation $y = 10.488x^2 -$ | $R^2$ | Predicted Toxin Conc. (ng/ml) (y)[c] |
|---|---|---|---|---|
| 800.000 | 28.715 | 784.98x + 14692 | 0.998 | 799.193 |
| 266.667 | 32.365 | ibid. | ibid. | 272.231 |
| 88.889 | 34.955 | ibid. | ibid. | 67.808 |
| 29.630 | 35.400 | $y = 7E+08x^{-4.7608}$ | 0.980 | 29.553 |
| 9.877 | 44.945 | ibid. | ibid. | 9.484 |
| 3.292 | 60.030 | ibid. | ibid. | 2.391 |
| 1.097 | 68.310 | $y = 5E+62x^{-34.157}$ | 0.999 | 1.093 |
| 0.366 | 70.650 | ibid. | ibid. | 0.346 |
| 0.122 | 72.845 | ibid. | ibid. | 0.122 |

[a]Standard purified *C. difficile* B toxin.
[b]Dye reduction rate by CHO-k1 cells incubated with the standard purified *C. difficile* toxin B for 20 hr. The dye reduction rate is calculated by using PM Analysis Software from 0 h to 3 h of incubation with Dye MB.
[c]Predicted *C. difficile* toxin B concentration calculated using the equation indicated in the table.

Figure 11B:
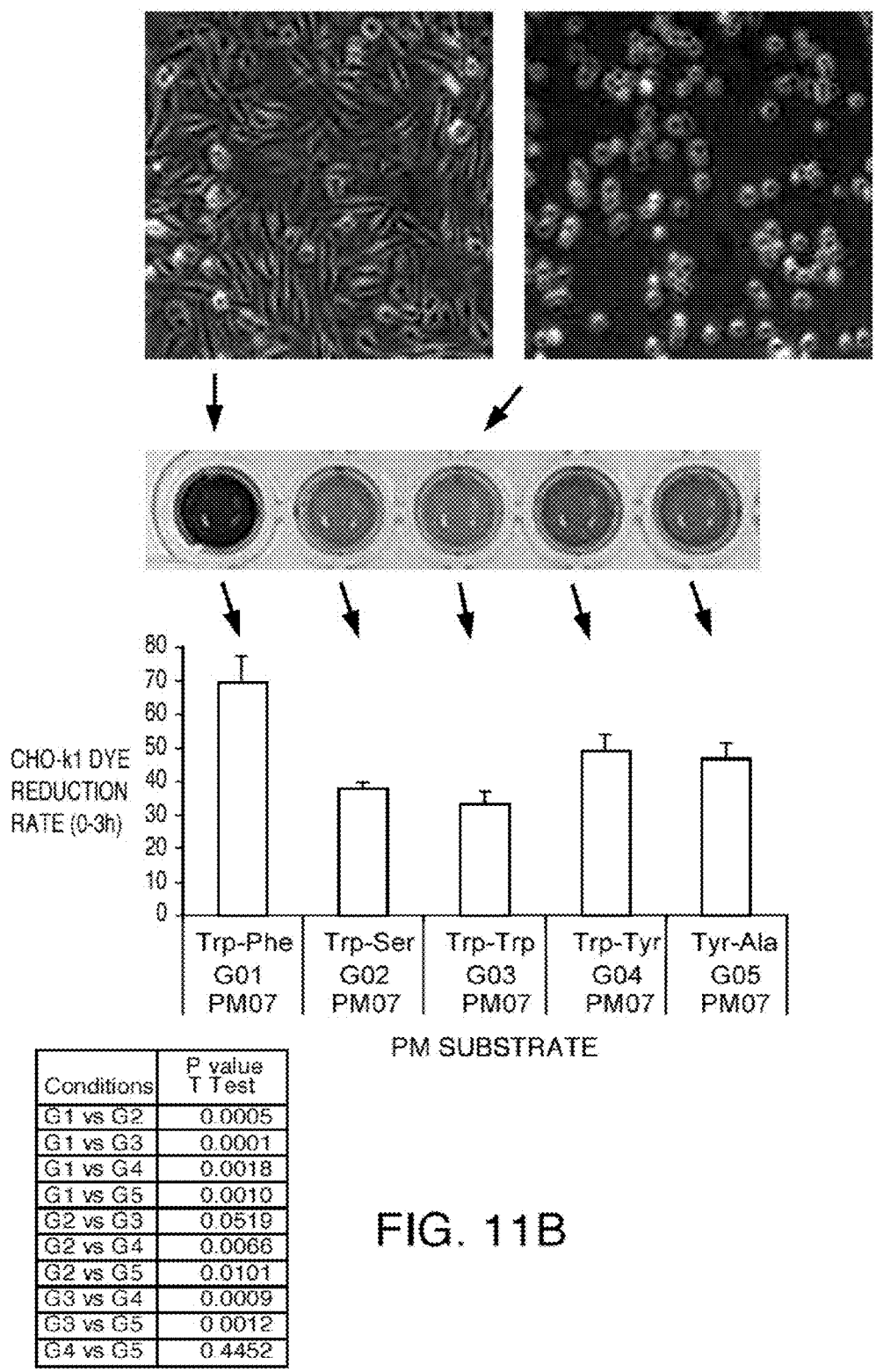
FIG. 11 presents exemplary data showing that cellular dye reduction is correlated to cell morphology changes induced by C. difficile toxin produced from PM culture conditions. A. CHO-k1 cells used in the assay. (a) Upper part: CHO-k1 cell morphological changes 20 h after exposure to C. difficile supernatants collected from different wells of PM1. A1=No PM substrate control; A3=N-Acetyl-D-Glucosamine; A9=D-Alanine; B2=D-Sorbitol. Lower part: corresponding cellular dye reduction by CHO-k1 cells. Pictures taken at the time points indicated after dye addition. (b) Upper panel: cellular dye reduction kinetics over the course of 24 h, automatically recorded by the OmniLog instrument. The numbers are averages of OmniLog Value (OmniLog Unit or Height); Lower panel: dye reduction rate over 0-3 h, an OmniLog parameter calculated and analyzed by PM Analysis Software. Larger rate numbers indicate faster dye reduction, and therefore healthier cells. (c) Upper panel: plots for OmniLog Values; Lower panel: plots for dye reduction rate. B. Similarities of changes seen with both CHO-k1 (left) and Vero (right) cells in cytotoxicity and dye reduction rate by C. difficile supernatants from individual wells of PM7.
Figure 11C:
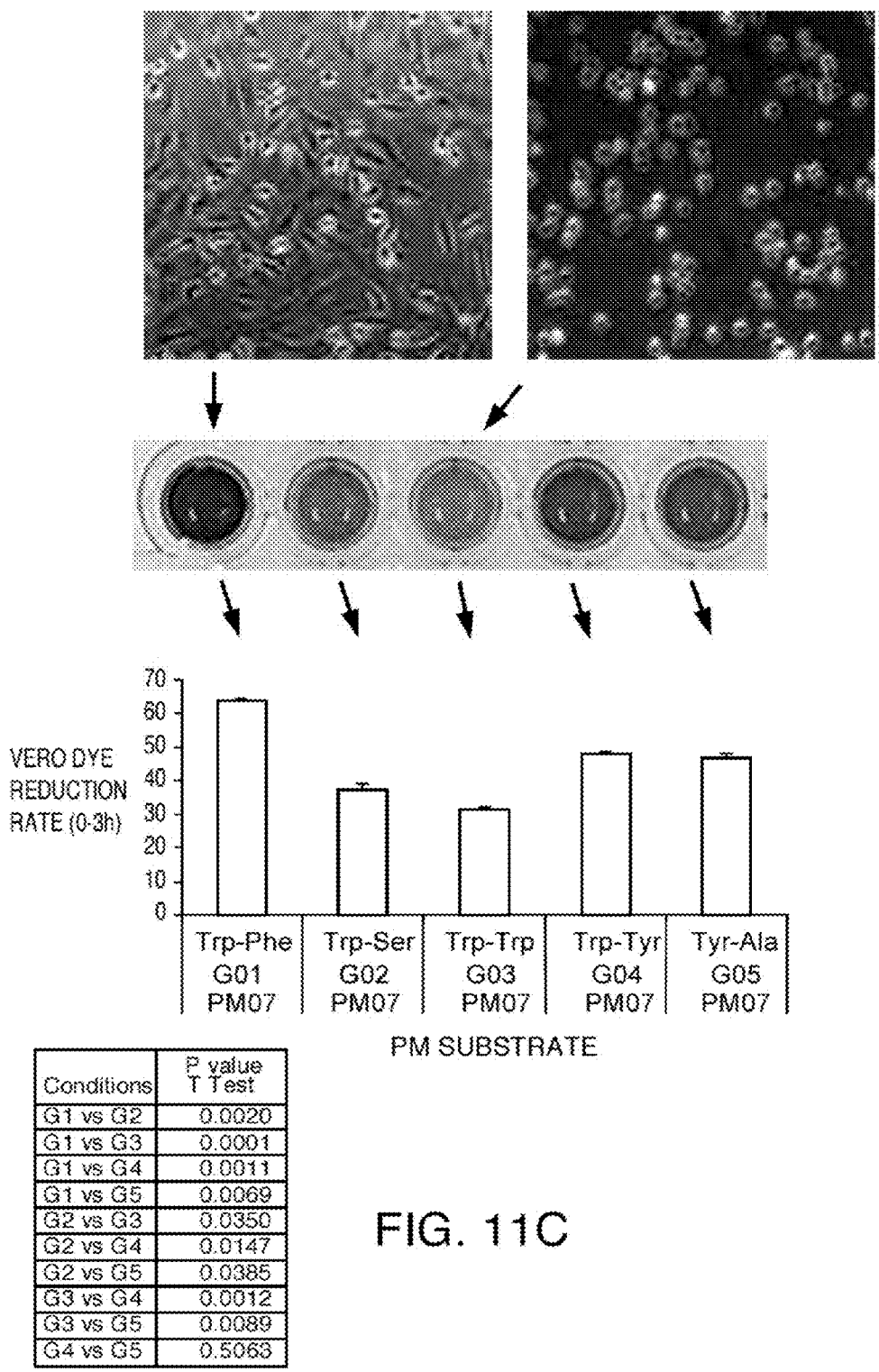
Figures 12A, 12B:
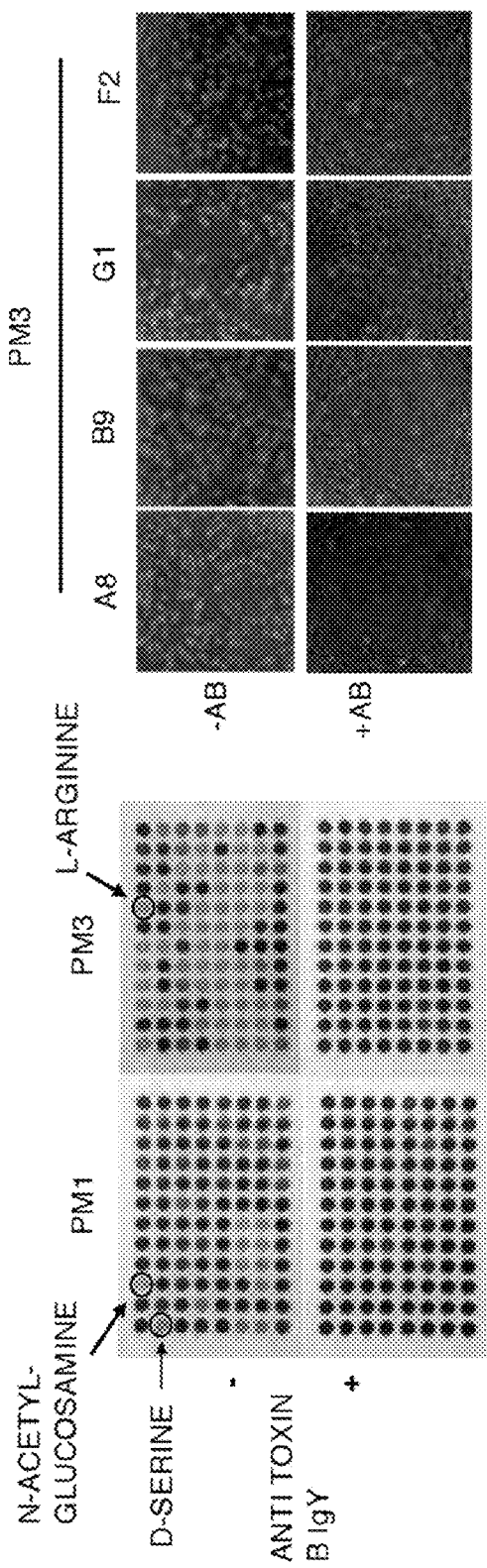
FIG. 12 presents exemplary data showing that cytotoxicity and neutralization assays of toxin prepared from C. difficile ATCC 9689 grown in PMs. Anti-toxin B polyclonal antibodies IgY were used throughout at 2.5 µg/ml for neutralization assays. A. Representative cell-based cytotoxicity and neutralization assays with redox dye MB in PMs 1 and 3 with CHO-k1 cells. B. Typical CHO-k1 cell morphological changes with or without anti-toxin B IgY. PM3: A8=L-Arginine, B9=L-Proline, G1=Xanthine, F2=Adenine. C. Dye reduction signals by CHO-k1 cells automatically and kinetically collected by OmniLog instrument. The numbers shown are means of dye reduction rates of replicas of each well in PM3, calculated by PM Analysis Software. D. Histograms of the same data of the dye reduction rates as in C. Tan: no C. difficile; Red: C. difficile; Green: C. difficile+ anti-toxin B IgY.
Figure 12C:
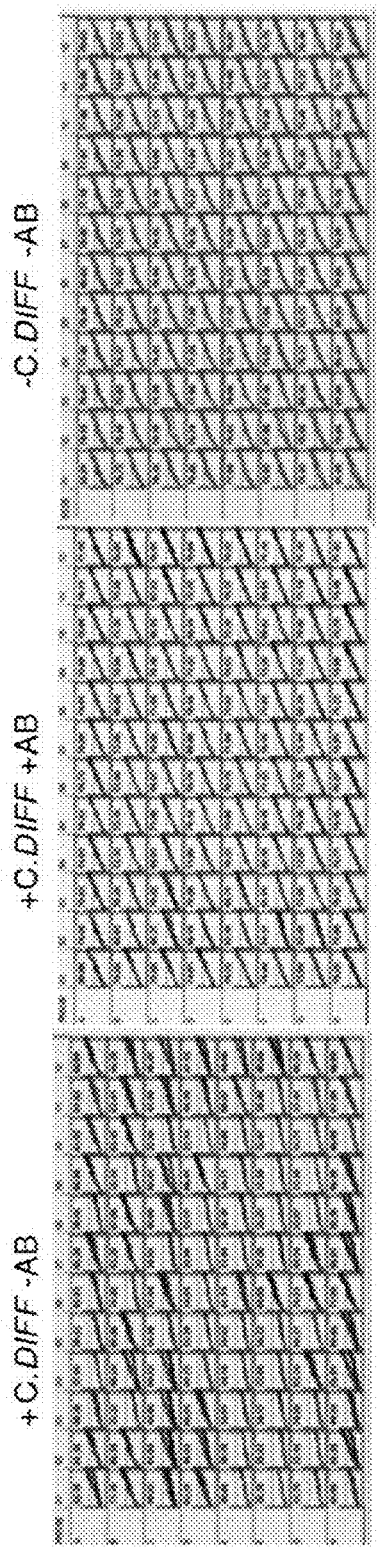
Figure 12D:
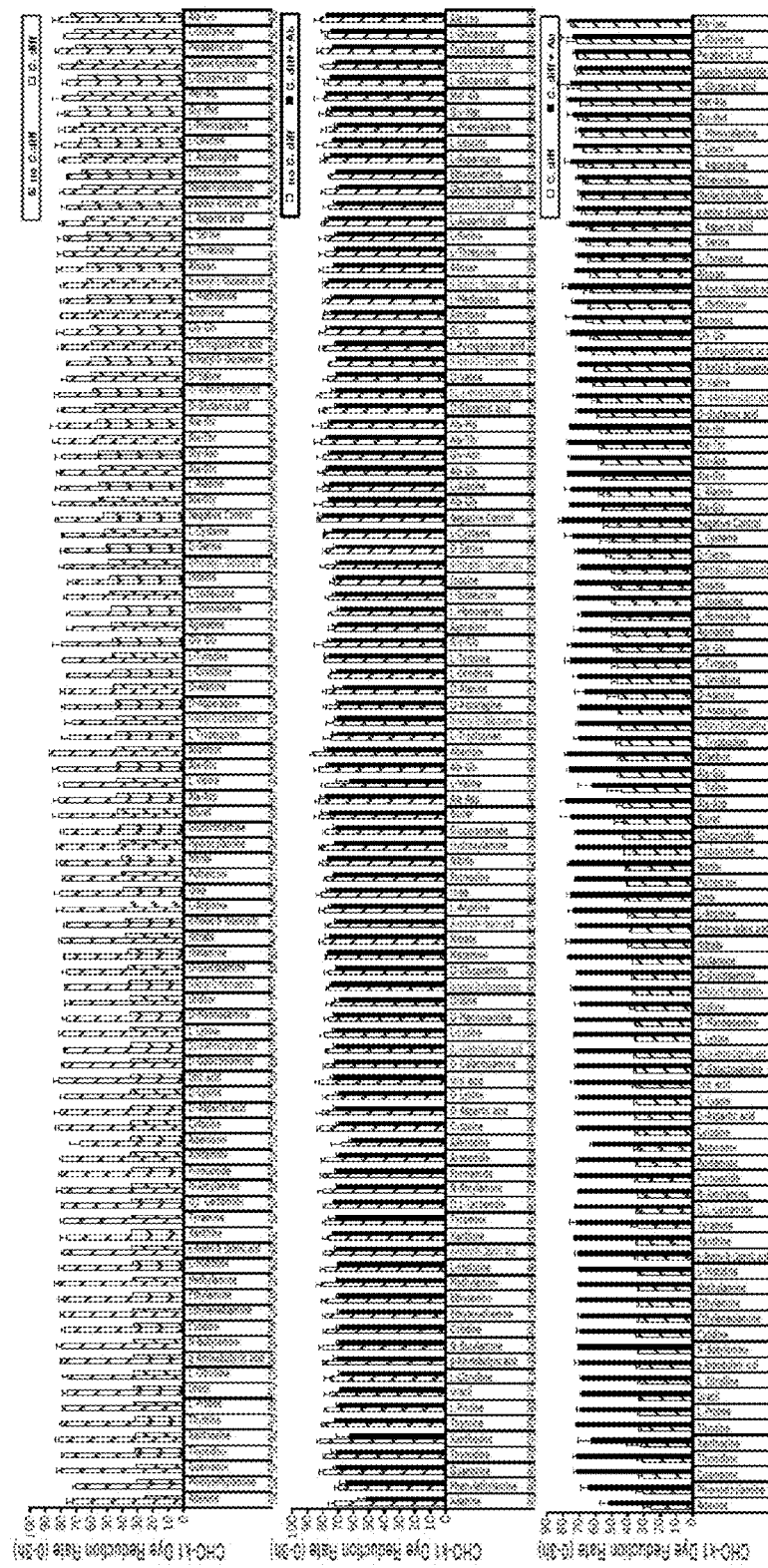

Toxin preparations taken directly from *C. difficile* cultures could intoxicate indicator cells and be effectively neutralized by anti-toxin B antibody. Both CHO-k1 and Vero cells were intoxicated by crude toxin preparations of *C. difficile* strain ATCC 9689 supernatants from different culture conditions of the PM panels. See, FIG. 11B. The morphological changes of the CHO-k1 cells were identical to those caused by purified standard toxin B. Compare, FIGS. 10A, 11A, 11B and 12B.

Screening Assay for Compounds that Inhibit *C. difficile* Toxin in 96-well Format.

Chemical containing panels PM 9-25, PM-M5, PM-M11-14 were rehydrated with Biolog IF-0a inoculating fluid. The panels were incubated at 37° C. for 24 hrs for complete rehydration of the chemicals. The chemical containing rehydrated solutions then were used to test their ability of inactivating *C. difficile* toxin B. Purified standard *C. difficile* toxin B (Listlab) was used in this screening. Based on the results of the standard toxin B titration against indicator cell line (CHO-k1 in this case), a single concentration of the toxin was chosen. Immediately before cell plating, the toxin was added to the cell suspension. After cell plating, five ul of each PM substrate were immediately added to each corresponding well. The cells were then incubated in $CO_2$ incubator at 37° C. for 20 hrs. Biolog Dye Mix MB was added to the cells at the end of the $CO_2$ incubation, which was immediately followed by incubation in Biolog OmniLog instrument at 36° C. for 3 hrs. The dye reduction occurred during the 3 hrs and the signals of dye reduction (color is darker when more dye molecules are reduced by the cells) were recorded automatically by the instrument. The healthier the cells are, the higher the dye reduction rate is, which indicates the inactivation of the toxin. Compared with no PM substrate controls, the toxin inactivating chemicals thus were easily identified after 3 hrs of dye reduction. The initial screening was followed by various confirmation experiments to reliably identified the promising candidates.

VII. Compounds that Inhibit Toxin Activity

Toxin B is a major toxin produced by pathogenic bacteria *Clostridium difficile*, which can damage, injure and/or kill mammalian cells. Counteracting this toxin is likely to be of clinical benefit. The data below show that by using an in vitro chemical screening method, protamine, polyarginines, and polylysines show specific activity that effectively inactivates *C. difficile* Toxin B.

Figure 4:
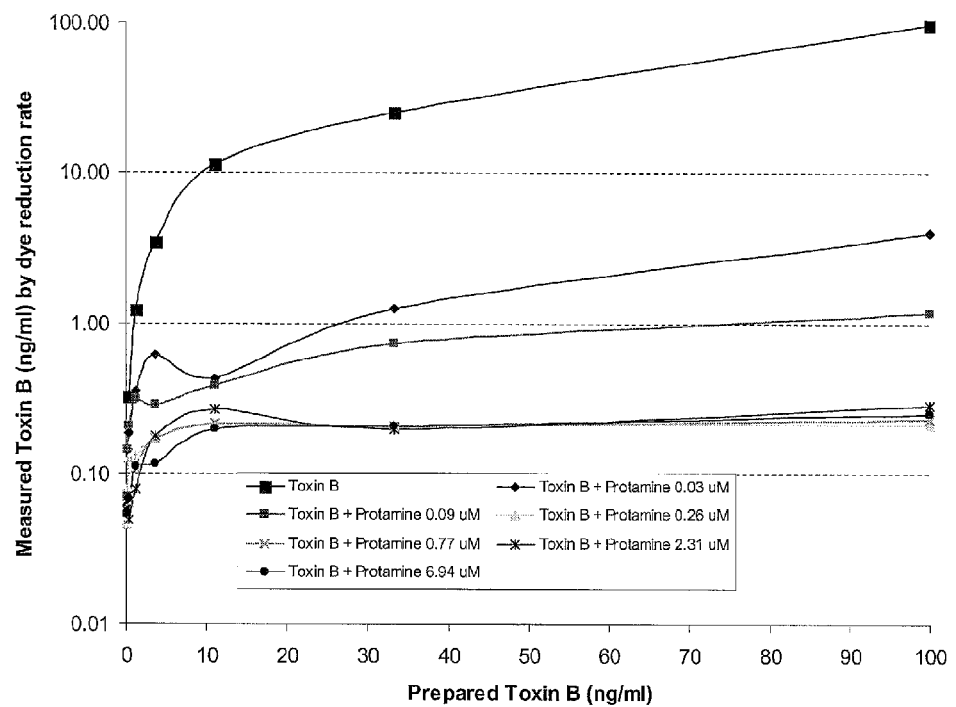
FIG. 4 presents the exemplary data of FIG. 2 replotted on a logarithmic scale.

The data below clearly show that these polypeptides are true anti-toxin B therapeutic agents and operate in a dose-dependant manner. The data also show that poly-L-lysine and poly-D-lysine are similar in potency against toxin B (protecting cells from being intoxicated) and similar in toxicity they have on the cultured cells. While protamine shows similar protective effects on the cells against toxin B, it is much less toxic to the cultured cells and has a wider range of safety concentrations as noted by the dose-dependent protective effect of protamine on the cells against different concentrations of toxin B. Optimal concentrations of protamine against various concentration of the toxin could be identified by this double dilution experiment. For example, 0.26 µM seems to be the optimal against toxin B. See FIG. 4.

A. Protamine

Native protamine has been reported to be comprised of four homogeneous peptides (e.g., Pro-1, Pro-2, Pro-3, and Pro-4). Chang et al., "Low molecular weight protamine (LMWP) as nontoxic heparin/low molecular weight heparin antidote (II): in vitro evaluation of efficacy and toxicity" *AAPS PharmSci*. 3:E18 (2001); and Liang et al., "A less toxic heparin antagonist—low molecular weight protamine" *Biochemistry (Mosc)* 68:16-120 (2003). The four protamine peptides have positively charged arginine-rich clusters and that are expected to bind to negatively charged molecules. See, FIG. 1. Elastase digestion of protamine has resulted in the detection of more than twenty low molecular weight protamine peptides (molecular weight ranging from 500 to 3000 Da). These peptides have been assigned to one of three groups (groups I-III) according to their molecular weights. See, Table I.

TABLE 1

Molecular Weights Of Protamine Peptide Groups

| Peptide | Molecular weight |
| --- | --- |
| I-1 | 1210.59; 1323.54; 1151.59 |
| I-2 | 1165.54; 1323.54; 1410.57; 1274.75 |
| II-1 | 1694.2 |
| II-2 | 1881.21 |
| II-3 | 2388.5 |
| II-4 | 2456.72 |
| II-5 | 2558.75 |
| III-1 | 2871.79 |
| III-2 | 2914.15 |
| Pro-1 | 4236.58 |
| Pro-2 | 4250.64 |
| Pro-3 | 4319.65 |
| Pro-4 | 4064.17 |

Protamine binding to heparin molecules suggest that their interaction is not simply due to non-specific electrostatic binding. This is because there was no relationship between binding stoichiometry and protamine peptide molecular weight, nor a correlation between binding stoichiometry and a heparin binding constant. Liang et al., "The minimal functional sequence of protamine" *Biochem. Biophys. Res. Comm.* 336:653-659 (2005). In one embodiment, the present invention contemplates a composition comprising the low molecular protamine peptide of peptide III-2. In one embodiment, peptide III-2 is derived from the protamine subunit Pro-2. In one embodiment, peptide III-2 is derived from the protamine subunit Pro-3. See, FIG. 1.

Figure 5:
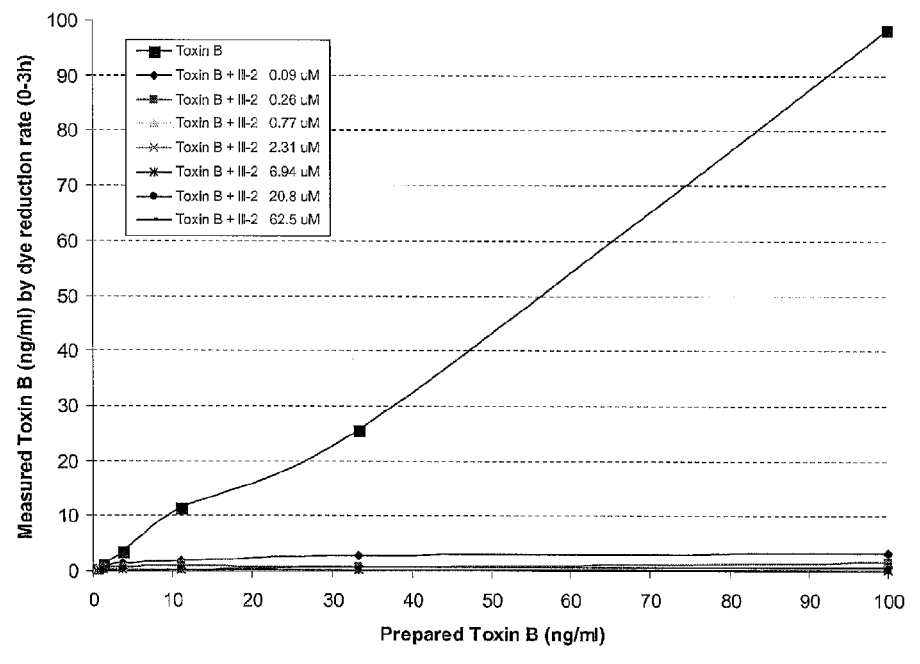
Figure 6:
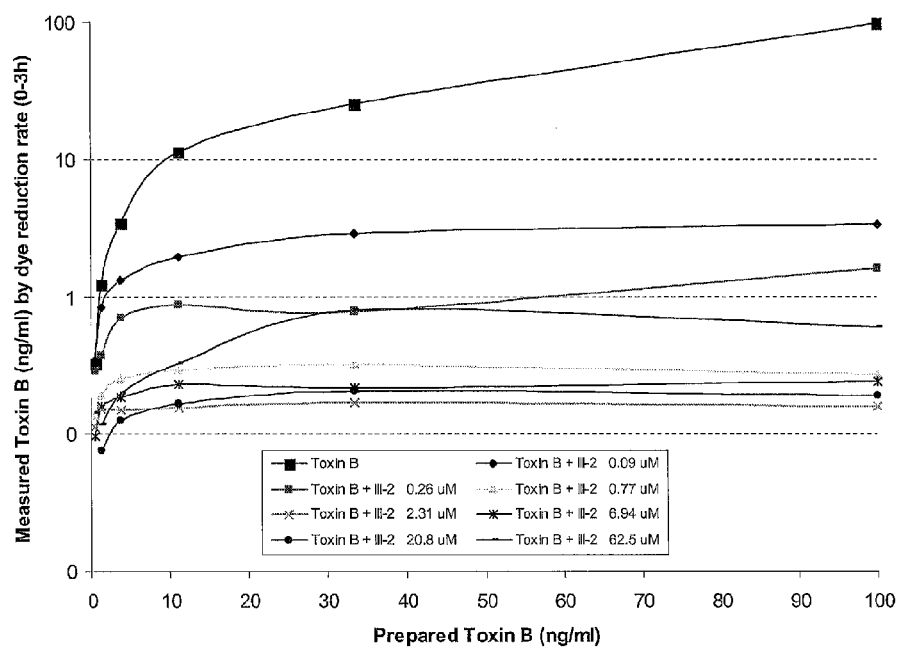
FIG. 6 presents the exemplary data of FIG. 4 replotted on a logarithmic scale.

The data presented herein show that protamine inactivates *Clostridium difficile* toxin B. See, FIG. 3. This dose response data demonstrates a very high selectivity of protamine for this toxin, as the toxin was completely inactivated at the lowest concentration of 0.03 µM. The data is replotted using a logarithmic scale to more clearly show the dose response relationship. See, FIG. 4. Similar results of complete *Clostridium difficile* toxin B inactivation was observed with the protamine III-2 peptide. See, FIGS. 5 and 6.

B. Polyarginine

Polyarginine is believed to be an arginine-rich, cell-penetrating polypeptide. Most likely, endocytosis mediates polyarginine's transit of the cell membrane. It has been suggested that chain length can mediate the electrostatic interaction of polyarginine with cell membrane anionic phospholipids. Takechi et al., "Physicochemical mechanism for the enhanced ability of lipid membrane penetration of polyarginine" *Langmuir* 27(11):7099-7107 (2011).

Figure 7:
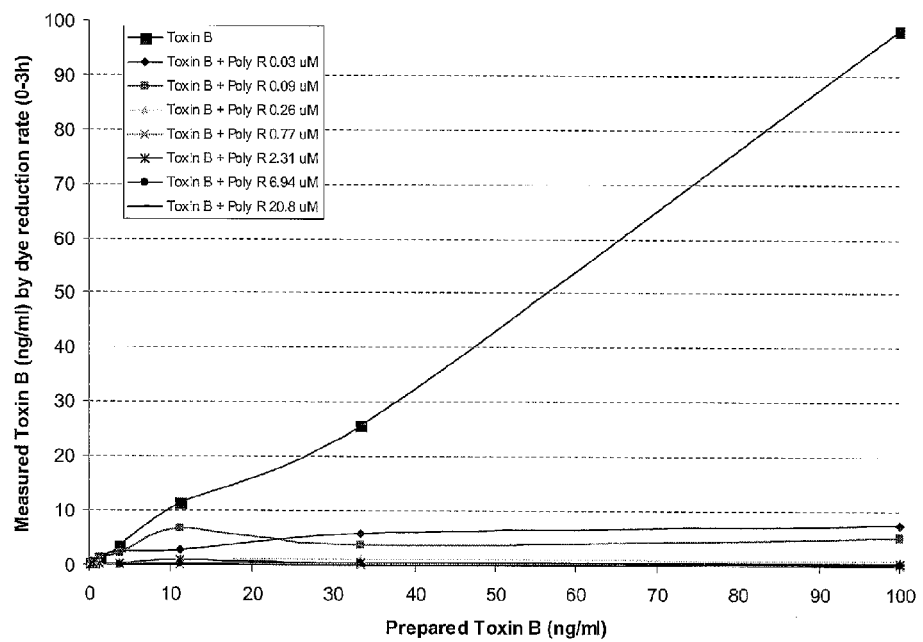
FIG. 7 presents exemplary data showing that polyarginine inactivates Clostria *difficile* Toxin B-mediated metabolic poisoning as measured by dye reduction assay. X-axis: actual (prepared) toxin B at 100 ng/ml, 33.3 ng/ml, 11.1 ng/ml, 3.7 ng/ml and 1.2 ng/ml; Y-axis: measured toxin B by dye reduction rate. Large Squares: Positive Control. Diamonds: Toxin B+0.03 μM polyarginine Small Squares: Toxin B+0.09 μM polyarginine. Triangle: Toxin B+0.26 μM polyarginine. Crosses: Toxin B+0.77 µM polyarginine. Hatched Crosses: Toxin B+2.31 µM polyarginine Circle: Toxin B+6.94 µM polyarginine. Half Square: Toxin B+20.8 µM polyarginine.
Figure 8:
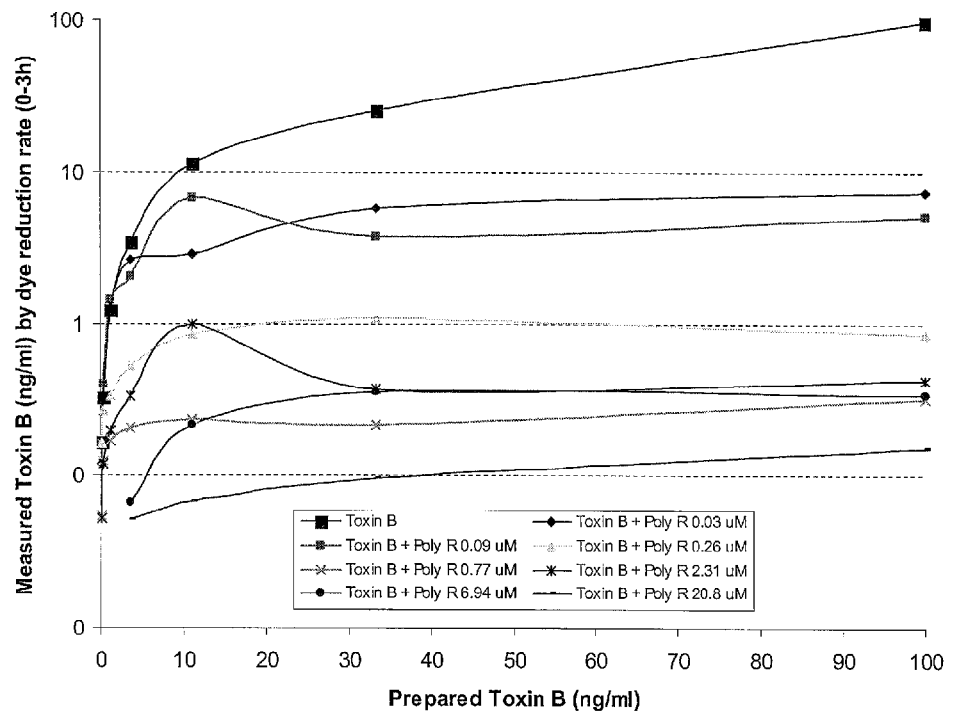
Figure 9A:
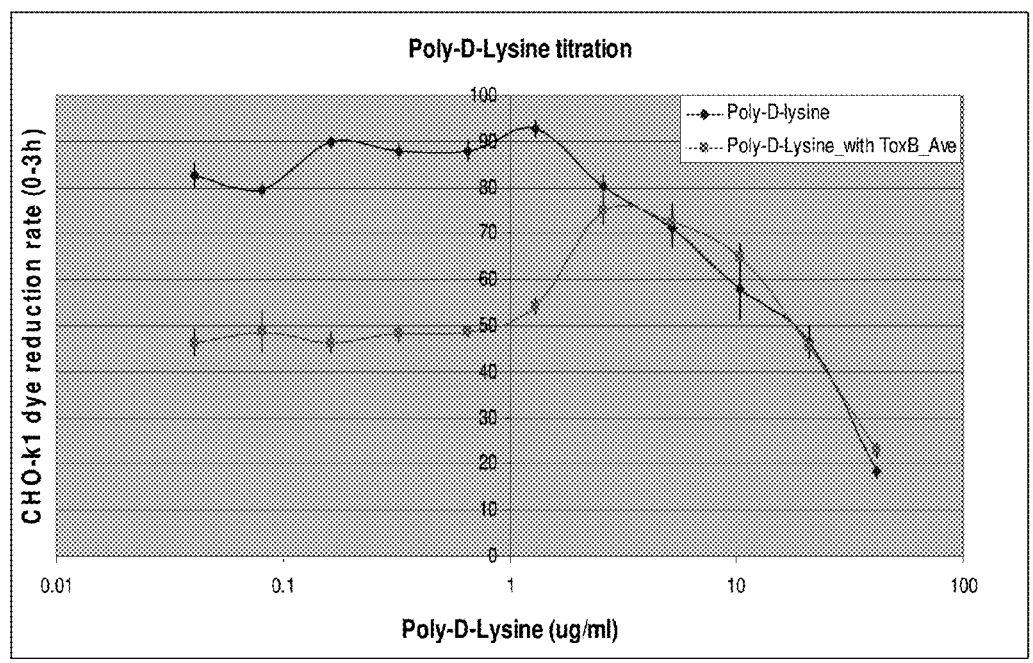
FIG. 9 presents exemplary data showing a dose-response relationship of C. difficile Toxin B inactivation with increasing concentrations of polylysine. Panels A & B: polylysine concentrations of 0.0420, 0.083, 0.166, 0.332, 0.664, 1.328, 2.656, 5.313, 10.63, 21.25, and 42.5 ug/ml.
Figure 9B:
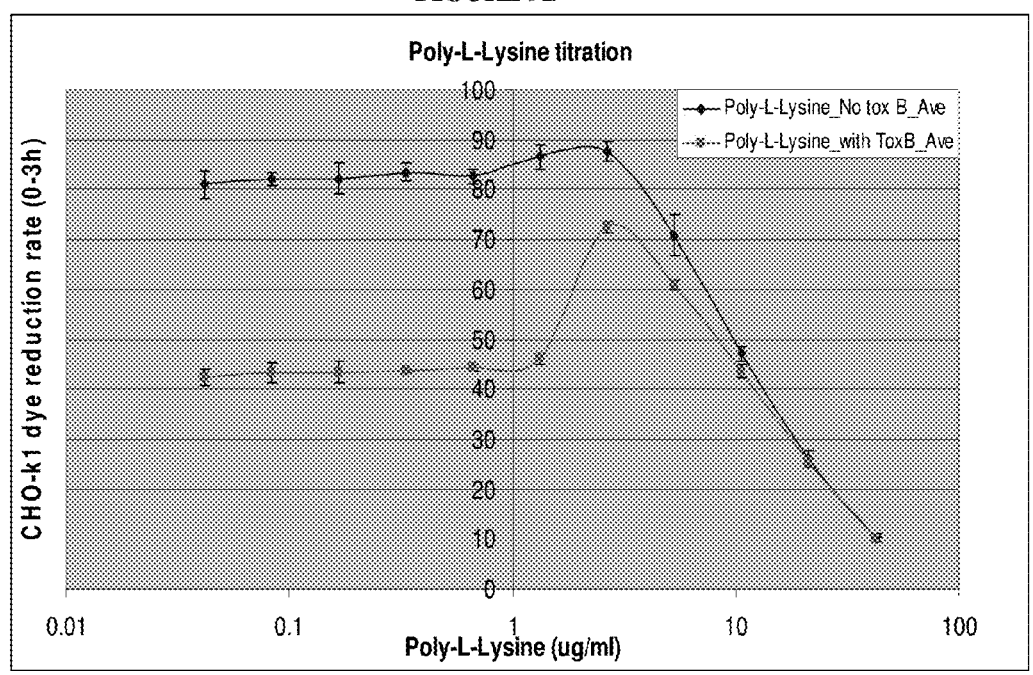

The data presented herein show that polyarginine inactivates *Clostridium difficile* toxin B. See, FIG. 7. This dose response data demonstrates a very high selectivity of polyarginine for this toxin, as the toxin was completely inactivated at the lowest concentration of 0.03 µM. The data is replotted using a logarithmic scale to more clearly show the dose response relationship. See, FIG. 8.

C. Polylysine Polylysine is a small natural homopolymer of the essential amino acid L-lysine that is produced naturally by bacterial fermentation. Polylysine is typically produced as a homo-polypeptide of approximately 25-30 L-lysine residues. Shima et al., "Polylysine produced by *Streptomyces*" *Agricultural and Biological Chemistry* 41:1807-1809 (1977). Polylysine belongs to the group of cationic polymers. In water, polylysine contains a positively charged hydrophilic amino group. Polylysine can be adsorbed electrostatically onto the cell surface of the bacteria, followed by a stripping of the outer membrane. This eventually may lead to an abnormal distribution of the cytoplasm causing damage to the bacterial cell. Shima et al., "Antimicrobial action of ∈-poly-L-lysine" *Journal of Antibiotics* 37(11):1449-1455 (1984). It has been reported that polylysine has an antimicrobial effect against yeast, fungi, Gram-positive bacteria and Gram-negative bacteria. Hiraki, J., "Basic and applied studies on ∈-polylysine" *Journal of Antibacterial Antifungal Agents* 23:349-354 (1995). Polylysine can also be branch-structured and used for DNA delivery: "DNA delivery with hyperbranched polylysine: A comparative study with linear and dendritic polylysine" *J Control Release* pii: S0168-3659(13)00046-1 (2013).

The data herein demonstrates that either poly-L-lysine or poly-D-lysine effectively inactivates 50 ng/ml *C. difficile* Toxin B. For example, a dose response microwell array assay with different concentrations of polylysine indicate significant toxin inactivation begins at a concentration of approximately 1 ug/ml. See, FIG. 9, Panels A & B, respectively. While both polylysines show some cytotoxicity when given alone at higher concentrations, a clear therapeutic window is evident at concentrations ranging between 1-10 ug/ml.

VIII. Compounds that Inhibit Toxin Production

Microbial toxin production is believed to play a role in the pathogenesis of *Clostridium difficile* and many other pathogenic microorganisms. For example, toxin synthesis can be influenced by a variety of known and unknown factors including, but not limited to, genetics, physiology, and/or environment.

Cationic amino acids lysine, asparagine, glutamic acid and glutamine have been reported to inhibit *C. difficile* growth and toxin production. However, these observations were made under artificial conditions by using a biotin-limited condition that is known to enhance *C. difficile* toxin production. Yamakawa et al., "Inhibition Of Enhanced Toxin Production By *Clostridium difficile* In Biotin-Limited Conditions" *J. Med. Microbiol.* 47:767-771 (1998). These conditions do not reflect in vivo environments. Consequently, such observations do not predict a direct interaction between a cationic peptide and bacterial toxin in the systemic circulation of a patient.

The data presented herein show that among the numerous different culture conditions that we tested, approximately eighty-nine (89) culture conditions resulted in a strong toxin induction while approximately thirty-one (31) culture conditions resulted in strong toxin repression. In one embodiment, culture conditions that resulted in a strong toxin induction included, but was not limited to, adenine, guanosine, arginine dipeptides, γ-D-Glu-Gly, and/or methylamine. In one embodiment, leucine dipeptides and the triple-leucine tripeptide resulted in strong toxin inhibition of toxin production.

In one embodiment, the present invention contemplates a method of modulating toxin production of *C. difficile* type strain ATCC 9689. In one embodiment, the method includes, but is not limited to, variations of basic cellular nutritional components for carbon, nitrogen, phosphorus, and sulfur (768 culture conditions, PM1-8). In one embodiment, the method may be used for all toxin-producing clostridia as well as toxin-producing aerobic bacteria.

The levels of toxin production in the microbial supernatants were distinctively different under different PM culture conditions. This is clearly shown both by: i) the cell culture toxicity assay (See, FIGS. 11A, 11B, 12B); and ii) the dye reduction assay with the indicator cells (FIGS. 11, 12A, 12C, 12D). As seen in the case of purified standard toxin B (FIG. 10), the inverse correlation between the CPE and dye reduction rate of the intoxicated cells was also observed with unpurified toxin preparations (filtered supernatants) from various PM culture conditions (FIG. 11). These adverse effects of unpurified toxin preparations on cell morphology and dye reduction were also specifically prevented by anti-toxin B IgY polyclonal antibodies. FIGS. 12A-D.

The cell mass under most PM culture conditions peaked at 24 h and thereafter tended to decrease at 48 h and further decrease at 72 h. In contrast, initial experiments indicated that toxin production was low at 24 h and tended to peak around 72 h (data not shown).

To examine the effect of culture conditions on toxin production, *C. difficile* ATCC 9689 was cultured in PM1-8 which constitutes 768 culture conditions with variations in the basic metabolic nutrients, C, N, P, and S for 72 h before toxin-containing supernatants were collected.

CHO-k1 cells treated with the 768 *C. difficile* supernatants showed different degrees of CPE. FIGS. 11A, 11B and 12B. Control experiments (no *C. difficile*) were also performed to show that the 768 chemicals themselves did not induce toxicity to the CHO-k1 cells (data not shown). There were 544 out of 768 culture conditions that significantly induced *C. difficile* toxin production (t-test, p≤0.05). See, Table 2.

TABLE 2

*C. difficile* toxin production ranges and statistics under different culture conditions from PM1-8

| Toxin concentration range (ng/ml)[a] | Number of PM conditions ($P < 0.05^b$) | Number of PM conditions ($P > 0.05^b$) | Total |
|---|---|---|---|
| >=420 | 89 | 0 | 89 |
| >=42, <420 | 192 | 10 | 202 |
| >2.562, <42 | 262 | 184 | 446 |
| <0.122[c] | 1 | 30 | 31 |
| Total | 544 | 224 | 768 |

[a]For measurable toxin levels, the numbers indicate toxin concentrations in supernatants of *C. difficile* grown under different PM conditions.
[b]The P values were obtained from t-test on the dye reduction rates by CHO-k1 cells in the presence vs absence of *C. difficile* supernatants collected from different PM conditions.
[c]Below the measurable limit in CHO-k1 cell assay medium of 0.122 ng/ml. Note that the concentration of the toxin in the cell assay medium is 21-fold diluted from the bacterial supernatant (see Materials and Methods).

Of these 544 culture conditions, 89 (16.4% of 544) induced toxin production at high levels of =>420 ng/ml (Table 3), 192 (35.3% of 544) gave a middle range level of =>42 but<420 ng/ml (Table 4), and 262 (48.2% of 544) gave a low range level of toxin production, >2.562 but<42 ng/ml in the supernatants (Table 2). There were 224 out of 768 culture conditions that were not statistically significant in inducing toxin production (P>0.05 except one PM7 A4 Leu-Trp, P=0.048). Of these 224, 30 (13.8% of 224) produced lowest toxin levels (<0.122 ng/ml in CHO-k1 cell assay medium, or possibly 0 ng/ml). Tables 2 and 5.

TABLE 3

PM substrates giving highest levels of toxin production by *C. difficile* ATCC 9689

| Plate panel | Well | Chemical | Category | *C. difficile* Mass[a] | Toxin (ng/ml)[b] | P value[c] |
|---|---|---|---|---|---|---|
| PM03 | F02 | Adenine | nucleobase | 0.031 | >16800 | 2.10E−04 |
| PM03 | F07 | Guanosine | nucleoside | 0.0092 | 10402 | 2.45E−05 |
| PM06 | B07 | Arg-Asp | dipeptide | 0.0444 | 10371 | 2.32E−07 |
| PM08 | G02 | γ-D-Glu-Gly | dipeptide, γ- | 0.0519 | 10122 | 3.34E−03 |
| PM06 | B05 | Arg-Ala | dipeptide | 0.0456 | 10080 | 5.70E−08 |
| PM03 | G02 | Xanthosine | nucleoside | 0.0516 | 9499 | 6.36E−09 |
| PM06 | B08 | Arg-Gln | dipeptide | 0.0476 | 8912 | 4.54E−08 |
| PM06 | C05 | Arg-Tyr | dipeptide | 0.0455 | 8819 | 7.07E−05 |
| PM06 | F10 | His-Pro | dipeptide | 0.0481 | 8568 | 6.08E−07 |
| PM06 | C04 | Arg-Trp | dipeptide | 0.0499 | 8423 | 7.81E−07 |
| PM08 | F04 | β-Ala-His | dipeptide, β- | 0.0473 | 8265 | 3.15E−06 |
| PM06 | B06 | Arg-Arg | dipeptide | 0.0435 | 8229 | 4.65E−07 |
| PM03 | F08 | Thymine | nucleobase | 0.0338 | 7749 | 2.83E−09 |
| PM06 | C03 | Arg-Ser | dipeptide | 0.0448 | 7608 | 1.85E−08 |
| PM07 | D08 | Pro-Hyp | dipeptide | 0.045 | 7523 | 1.04E−06 |
| PM03 | F09 | Thymidine | nucleoside | 0.0384 | 7336 | 3.22E−08 |
| PM07 | E07 | Ser-Pro | dipeptide | 0.0472 | 7136 | 2.23E−07 |
| PM06 | F08 | His-Lys | dipeptide | 0.0453 | 6993 | 1.02E−07 |
| PM06 | C02 | Arg-Phe | dipeptide | 0.0467 | 6541 | 2.70E−07 |
| PM03 | D05 | Methylamine | amine | 0.0398 | 6537 | 1.61E−04 |
| PM07 | F07 | Trp-Arg | dipeptide | 0.0628 | 6468 | 9.53E−07 |
| PM03 | G08 | γ-Aminobutyric acid | amino fatty acid, γ-, GABA | 0.0375 | 6329 | 4.45E−11 |
| PM03 | D07 | N-Butylamine | amine, N- | 0.0407 | 5679 | 3.74E−04 |
| PM07 | A07 | Lys-Arg | dipeptide | 0.0502 | 5536 | 5.20E−06 |
| PM03 | B09 | L-Proline | amino acid | 0.0394 | 5343 | 1.07E−10 |
| PM07 | B04 | Lys-Trp | dipeptide | 0.006 | 5277 | 5.29E−06 |
| PM07 | B02 | Lys-Ser | dipeptide | 0.0426 | 5105 | 1.25E−07 |
| PM03 | F05 | Cytosine | nucleobase | 0.0361 | 4809 | 1.11E−09 |
| PM07 | F05 | Thr-Pro | dipeptide | 0.0355 | 4772 | 3.32E−06 |
| PM03 | G03 | Uric acid | nucleobase derivative | 0.0556 | 4289 | 6.27E−07 |
| PM03 | D10 | Ethylenediamine | amine | 0.0369 | 4133 | 2.78E−05 |
| PM07 | G03 | Trp-Trp | dipeptide | 0.055 | 4104 | 1.74E−03 |
| PM06 | B09 | Arg-Glu | dipeptide | 0.0404 | 4059 | 1.70E−09 |
| PM03 | F04 | Cytidine | nucleoside | 0.0456 | 3952 | 9.78E−12 |
| PM03 | D08 | Ethylamine | amine | 0.0401 | 3799 | 8.84E−05 |
| PM06 | E11 | Gly-Pro | dipeptide | 0.0414 | 3798 | 9.96E−07 |
| PM03 | B03 | L-Histidine | amino acid | 0.0361 | 3640 | 8.27E−05 |
| PM03 | E05 | Formamide | amide | 0.0418 | 3639 | 1.96E−11 |
| PM06 | F02 | Gly-Trp | dipeptide | 0.0431 | 3632 | 1.68E−05 |
| PM03 | G09 | ε-Amino-N-Caproic acid | amino fatty acid, ε- | 0.0366 | 3389 | 4.02E−05 |
| PM03 | D06 | N-Amylamine | amine, N- | 0.0433 | 3384 | 9.99E−09 |
| PM03 | C05 | D-Aspartic acid | amino acid, D- | 0.0109 | 3334 | 3.33E−04 |
| PM03 | F10 | Uracil | nucleobase | 0.0375 | 3204 | 2.32E−04 |
| PM03 | C10 | L-Citrulline | amino acid | 0.0377 | 3086 | 1.56E−03 |
| PM08 | C11 | Pro-Arg | dipeptide | 0.0442 | 2967 | 2.61E−03 |
| PM03 | E04 | Acetamide | amide | 0.0458 | 2926 | 7.25E−09 |
| PM03 | E07 | D,L-Lactamide | amide, DL- | 0.04 | 2859 | 1.50E−07 |
| PM03 | E03 | Tyramine | amine, Tyr derivative | 0.0442 | 2772 | 9.91E−07 |
| PM01 | F04 | D-Threonine | amino acid, D- | 0.0923 | 2699 | 1.04E−03 |
| PM01 | A03 | N-Acetyl-D-Glucosamine | acetyl amino sugar, N- | 0.0955 | 2657 | 5.17E−05 |
| PM01 | G05 | L-Alanine | amino acid | 0.113 | 2469 | 1.02E−04 |
| PM01 | F05 | Fumaric Acid | carboxylic acid | 0.018 | 2284 | 8.73E−04 |
| PM03 | E02 | β-Phenylethylamine | amine, Phe derivative, β- | 0.0448 | 2147 | 1.80E−06 |
| PM01 | G06 | Ala-Gly | dipeptide | 0.0934 | 2130 | 4.82E−07 |
| PM03 | G01 | Xanthine | nucleobase | 0.2978 | 2079 | 2.83E−05 |
| PM08 | C01 | Lys-Gly | dipeptide | 0.047 | 1950 | 1.30E−04 |
| PM08 | H03 | Gly-Gly-Gly | tripeptide | 0.0456 | 1811 | 2.93E−05 |
| PM03 | B06 | L-Lysine | amino acid | 0.0436 | 1767 | 3.75E−04 |
| PM03 | E09 | D-Galactosamine | amino sugar, D- | 0.0374 | 1723 | 3.43E−09 |
| PM08 | F03 | β-Ala-Gly | dipeptide, β- | 0.0389 | 1547 | 2.32E−07 |
| PM01 | G03 | L-Serine | amino acid | 0.0635 | 1537 | 4.48E−03 |
| PM08 | G04 | Gly-D-Asp | dipeptide | 0.0467 | 1537 | 3.45E−07 |
| PM01 | F01 | Gly-Asp | dipeptide | 0.1004 | 1507 | 3.62E−03 |
| PM03 | C07 | D-Lysine | amino acid, D- | 0.0489 | 1472 | 1.00E−04 |
| PM03 | G10 | D,L-α-Amino-Caprylic acid | amino fatty acid, DL-α | 0.0484 | 647 | 4.73E−07 |
| PM01 | F06 | Bromosuccinic Acid | carboxylic acid | 0.0335 | 615 | 8.93E−05 |
| PM01 | B01 | D-Serine | amino acid, D- | 0.1114 | 588 | 1.19E−03 |

TABLE 3-continued

PM substrates giving highest levels of toxin production by *C. difficile* ATCC 9689

| Plate panel | Well | Chemical | Category | *C. difficile* Mass[a] | Toxin (ng/ml)[b] | P value[c] |
|---|---|---|---|---|---|---|
| PM02 | G07 | L-Homoserine | amino acid, Thr isomer | 0.0071 | 587 | 7.04E−03 |
| PM03 | E10 | D-Mannosamine | amino sugar, D- | 0.0364 | 583 | 1.06E−05 |
| PM08 | G12 | D-Ala-Gly-Gly | tripeptide | 0.0538 | 515 | 1.09E−05 |
| PM02 | G10 | L-Leucine | amino acid | 0.089 | 503 | 2.97E−05 |
| PM03 | E01 | Histamine | amine, His derivative | 0.0424 | 492 | 3.79E−08 |
| PM03 | F11 | Uridine | nucleoside | 0.0373 | 484 | 2.62E−04 |
| PM03 | E08 | D-Glucosamine | amino sugar, D- | 0.0447 | 476 | 3.86E−06 |
| PM03 | A08 | L-Arginine | amino acid | 0.046 | 458 | 2.65E−05 |
| PM03 | G11 | δ-Amino-N-Valeric acid | amino fatty acid, δ- | 0.0424 | 435 | 5.08E−10 |
| PM1-8 | All wells | All substrates | control | 0.0517 | 50 | 3.62E−02 |
| PM1-8 | A1 | No substrate | control | 0.0517 | 44 | 9.80E−02 |

[a]OD (750 nm) difference between *C. difficile* under certain PM substrate and the same substrate without *C. difficile*.
[b]Toxin concentrations in *C. difficile* supernatant collected from different PM conditions, which were calculated from the average dye reduction rate by the CHO-k1 cells according to the equations in Table 1.
[c]The P values were obtained from t-test on the dye reduction rates of CHO-k1 cells in the presence or absence of *C. difficile* supernatants collected from different PM conditions.

TABLE 4

PM substrates giving middle levels of toxin productions by *C. difficile* ATCC 9689

| Plate panel | Well | Chemical | Category | *C. difficile* Mass[a] | Toxin (ng/ml)[b] | P value[c] |
|---|---|---|---|---|---|---|
| PM07 | F06 | Trp-Ala | dipeptide | 0.0489 | 415 | 1.08E−04 |
| PM03 | A03 | Nitrite | inorganic N-source | 0.0333 | 383 | 3.24E−07 |
| PM08 | B08 | Leu-Asn | dipeptide | 0.0482 | 381 | 2.24E−03 |
| PM06 | F07 | His-Leu | dipeptide | 0.0495 | 376 | 6.77E−05 |
| PM03 | F03 | Adenosine | nucleoside | 0.0472 | 373 | 7.02E−03 |
| PM01 | G01 | Gly-Glu | dipeptide | 0.0411 | 366 | 5.53E−04 |
| PM06 | E03 | Gly-Arg | dipeptide | 0.0403 | 352 | 6.87E−05 |
| PM08 | B12 | Lys-Asp | dipeptide | 0.0525 | 335 | 4.93E−05 |
| PM03 | D11 | Putrescine | amine | 0.0339 | 335 | 7.69E−08 |
| PM03 | G05 | Allantoin | nucleobase derivative | 0.0425 | 334 | 1.48E−08 |
| PM03 | D04 | Hydroxylamine | inorganic base, reducing agent | 0.0228 | 334 | 1.58E−07 |
| PM01 | D02 | D-Aspartic Acid | amino acid, D-Asp | 0.0269 | 331 | 5.56E−05 |
| PM02 | B02 | N-Acetyl-Neuraminic acid | acetyl amino sugar, sialic acid | 0.1163 | 328 | 1.77E−03 |
| PM04 | C12 | Cytidine 3',5'-Cyclic Monophosphate | nucleotide, 3',5'-cyclic | 0.0106 | 321 | 8.83E−05 |
| PM03 | A06 | Biuret | amide, carbamide derivative | 0.0394 | 307 | 3.59E−06 |
| PM01 | G10 | Methylpyruvate | carboxylic acid derivative, methyl ester | 0.0795 | 299 | 5.31E−05 |
| PM08 | H08 | Gly-Phe-Phe | tripeptide | 0.2751 | 298 | 4.18E−07 |
| PM08 | G05 | Gly-D-Ser | dipeptide | 0.0543 | 297 | 8.49E−06 |
| PM08 | H07 | Val-Tyr-Val | tripeptide | 0.0382 | 296 | 2.62E−06 |
| PM03 | E06 | Glucuronamide | sugar acid, amide (6c) | 0.0369 | 280 | 1.10E−06 |
| PM07 | A08 | Lys-Glu | dipeptide | 0.0425 | 271 | 1.01E−04 |
| PM01 | G04 | L-Threonine | amino acid, Thr | 0.0643 | 243 | 3.70E−03 |
| PM07 | H05 | Val-Asp | dipeptide | 0.0469 | 225 | 1.12E−04 |
| PM03 | C02 | L-Valine | amino acid, Val | 0.0431 | 223 | 2.01E−04 |
| PM08 | H05 | Gly-Gly-Leu | tripeptide | 0.0305 | 215 | 1.03E−04 |
| PM02 | B08 | Arbutin | sugar hydroquinone (12c), glycoside | 0.128 | 213 | 5.36E−05 |
| PM03 | C04 | D-Asparagine | amino acid, D-Apn | 0.0321 | 196 | 2.31E−04 |
| PM07 | E04 | Ser-Leu | dipeptide | 0.0404 | 187 | 3.43E−04 |
| PM07 | G05 | Tyr-Ala | dipeptide | 0.0331 | 186 | 5.79E−05 |
| PM03 | H10 | Gly-Glu | dipeptide | 0.0472 | 184 | 5.43E−03 |
| PM08 | E03 | Trp-Val | dipeptide | 0.0276 | 184 | 1.26E−04 |
| PM08 | E12 | Val-Pro | dipeptide | 0.0425 | 183 | 2.01E−04 |
| PM06 | F12 | His-Trp | dipeptide | 0.0442 | 178 | 1.49E−04 |
| PM08 | E08 | Val-Glu | dipeptide | 0.0481 | 178 | 1.11E−05 |
| PM07 | H02 | Tyr-Tyr | dipeptide | 0.0415 | 174 | 2.16E−04 |
| PM01 | H12 | 2-Aminoethanol | amine, alcohol, 2- | 0.0853 | 173 | 1.15E−03 |
| PM03 | C01 | L-Tyrosine | amino acid, Tyr | 0.1528 | 172 | 1.52E−05 |
| PM03 | C03 | D-Alanine | amino acid, D-Ala | 0.038 | 171 | 1.70E−04 |
| PM03 | B12 | L-Tryptophan | amino acid, Trp | 0.0299 | 165 | 2.91E−04 |
| PM02 | E01 | Capric acid | fatty acid | 0.014 | 162 | 3.24E−04 |

TABLE 4-continued

PM substrates giving middle levels of toxin productions by *C. difficile* ATCC 9689

| Plate panel | Well | Chemical | Category | *C. difficile* Mass[a] | Toxin (ng/ml)[b] | P value[c] |
|---|---|---|---|---|---|---|
| PM02 | A06 | Dextrin | sugar, polysaccharide | 0.0478 | 162 | 3.99E−03 |
| PM08 | G06 | Gly-D-Thr | dipeptide | 0.0549 | 157 | 3.21E−05 |
| PM03 | E12 | N-Acetyl-D-Galactosamine | acetyl amino sugar, N- | 0.0355 | 153 | 3.06E−04 |
| PM07 | A11 | Lys-Lys | dipeptide | 0.0427 | 150 | 5.07E−05 |
| PM03 | C12 | L-Ornithine | amino acid, Orn | 0.0369 | 141 | 3.49E−04 |
| PM02 | D02 | Salicin | sugar phenol, β-glucoside (13c) | 0.1291 | 140 | 3.61E−03 |
| PM02 | C04 | D-Lyxose | sugar (5c), D- | 0.1508 | 139 | 3.82E−03 |
| PM03 | D02 | N-Phthaloyl-L-Glutamic acid | amino acid derivative | 0.0344 | 137 | 4.69E−05 |
| PM02 | H04 | L-Valine | amino acid, Val | 0.0917 | 135 | 1.28E−02 |
| PM07 | G04 | Trp-Tyr | dipeptide | 0.0451 | 134 | 5.89E−05 |
| PM02 | E02 | Caproic acid | fatty acid | 0.0568 | 133 | 1.90E−03 |
| PM02 | G12 | L-Methionine | amino acid, Met | 0.0818 | 127 | 6.01E−04 |
| PM06 | G04 | Ile-Arg | dipeptide | 0.0442 | 122 | 3.82E−03 |
| PM03 | A01 | Negative Control | negative control | 0.0403 | 122 | 1.90E−04 |
| PM03 | B04 | L-Isoleucine | amino acid, Ile | 0.0563 | 122 | 9.75E−04 |
| PM02 | D06 | D-Tagatose | sugar (6c), D- | 0.138 | 121 | 8.44E−04 |
| PM03 | C11 | L-Homoserine | amino acid, Thr isomer | 0.0293 | 119 | 2.52E−05 |
| PM01 | A09 | D-Alanine | amino acid, D-Ala | 0.1233 | 118 | 9.72E−06 |
| PM07 | A03 | Leu-Ser | dipeptide | 0.037 | 116 | 1.51E−04 |
| PM03 | C08 | D-Serine | amino acid, D-Ser | 0.0465 | 110 | 7.29E−05 |
| PM03 | A11 | L-Cysteine | amino acid, Cys | 0.0394 | 108 | 6.64E−05 |
| PM03 | D12 | Agmatine | amine, Arg derivative | 0.043 | 108 | 3.06E−04 |
| PM01 | C07 | D-Fructose | sugar (6c), D- | 0.1435 | 106 | 1.34E−06 |
| PM01 | H08 | Pyruvic Acid | carboxylic acid, α-keto acid | 0.093 | 103 | 5.67E−04 |
| PM02 | H02 | L-Phenylalanine | amino acid, Phe | 0.0714 | 103 | 2.46E−02 |
| PM1-8 | All wells | All substrates | control | 0.0517 | 50 | 3.62E−02 |
| PM1-8 | A1 | No substrate | control | 0.0517 | 44 | 9.80E−02 |

[a]OD (750 nm) difference between *C. difficile* under certain PM substrate and the same substrate without *C. difficile*.
[b]Toxin concentrations in *C. difficile* supernatant collected from different PM conditions, which were calculated from the average dye reduction rate by the CHO-k1 cells according to the equations in Table 1.
[c]The P values were obtained from t-test on the dye reduction rates of CHO-k1 cells in the presence or absence of *C. difficile* supernatants collected from different PM conditions.

TABLE 5

PM substrates giving lowest levels of toxin production by *C. difficile* ATCC 9689

| PM panel | Well | Chemical | Category | *C. difficile* mass[a] | Toxin (ng/ml)[b] | P value[c] |
|---|---|---|---|---|---|---|
| PM01 | H11 | β-Phenylethylamine | amine, Phe derivative, β-, (C-source) | 0.0477 | <0.122 | 9.40E−01 |
| PM02 | H11 | 2,3-Butanone | ketone, methyl ethyl, 2,3-, C-source) | 0.0572 | <0.122 | 4.87E−01 |
| PM04 | A01 | Negative Control | ctrl, no substrate | 0.0473 | <0.122 | 2.59E−01 |
| PM04 | A10 | Adenosine 5'-Monophosphate | nucleotide, (P-source) | 0.0495 | <0.122 | 8.02E−02 |
| PM04 | A03 | Pyrophosphate | diphosphate, (P-source) | 0.0075 | <0.122 | 1.98E−01 |
| PM04 | A04 | Trimetaphosphate | metaphosphate, (P-source) | 0.0493 | <0.122 | 1.86E−01 |
| PM04 | B01 | Thiophosphate | thiophosphate (P-source) | 0.0373 | <0.122 | 1.92E−01 |
| PM04 | H04 | D,L-Lipoamide | amide, 6,8-dithiooctanoic, DL-, (S-source) | 0.0265 | <0.122 | 1.16E−01 |
| PM04 | G12 | L-Methionine Sulfone | amino acid derivative (S-source) | 0.0446 | <0.122 | 3.84E−01 |
| PM04 | H06 | Taurine | aminoethanesulfonic acid, 2-, (S-source) | 0.0505 | <0.122 | 1.76E−01 |
| PM04 | H05 | Taurocholic acid | cholyltaurine (S-source) | 0.0536 | <0.122 | 1.64E−01 |
| PM04 | H08 | p-Aminobenzene Sulfonic acid | sulfanilic acid, p-, (S-source) | 0.0485 | <0.122 | 1.64E−01 |
| PM04 | H07 | Hypotaurine | sulfinic acid, (S-source) | 0.0438 | <0.122 | 3.83E−01 |
| PM04 | H12 | Tetramethylene Sulfone | Sulfone, (S-source) | 0.0442 | <0.122 | 6.03E−01 |
| PM04 | H09 | Butane Sulfonic acid | sulfonic acid derivative, (S-source) | 0.0398 | <0.122 | 3.37E−01 |
| PM04 | H10 | 2-Hydroxyethane Sulfonic acid | sulfonic acid derivative, 2-(S-source) | 0.0428 | <0.122 | 2.03E−01 |
| PM05 | A11 | Adenosine | nucleoside (nutritional stimulant) | 0.0414 | <0.122 | 5.88E−01 |

TABLE 5-continued

PM substrates giving lowest levels of toxin production by C. difficile ATCC 9689

| PM panel | Well | Chemical | Category | C. difficile mass$^a$ | Toxin (ng/ml)$^b$ | P value$^c$ |
|---|---|---|---|---|---|---|
| PM06 | A12 | Ala-Pro | dipeptide (N-source) | 0.0507 | <0.122 | 2.44E-01 |
| PM08 | H04 | Gly-Gly-Ile | tripeptide (N-source) | 0.0421 | <0.122 | 1.38E-01 |
| PM06 | E12 | Gly-Ser | dipeptide (N-source) | 0.0471 | <0.122 | 3.13E-01 |
| PM06 | H09 | Leu-Ile | dipeptide (N-source) | 0.0523 | <0.122 | 8.95E-02 |
| PM06 | H10 | Leu-Leu | dipeptide (N-source) | 0.0530 | <0.122 | 1.06E-01 |
| PM08 | H10 | Leu-Leu-Leu | tripeptide (N-source) | 0.0463 | <0.122 | 1.24E-01 |
| PM06 | H11 | Leu-Met | dipeptide (N-source) | 0.0501 | <0.122 | 1.12E-01 |
| PM06 | H12 | Leu-Phe | dipeptide (N-source) | 0.0538 | <0.122 | 7.52E-02 |
| PM07 | A04 | Leu-Trp | dipeptide (N-source) | 0.0380 | <0.122 | 4.79E-02 |
| PM07 | A02 | L-Glutamine | amino acid (N-source) | 0.0339 | <0.122 | 7.04E-02 |
| PM07 | A12 | Lys-Phe | dipeptide (N-source) | 0.0533 | <0.122 | 6.40E-02 |
| PM08 | D12 | Thr-Gln | dipeptide (N-source) | 0.0403 | <0.122 | 7.74E-02 |
| PM07 | G12 | Tyr-Phe | dipeptide (N-source) | 0.0559 | <0.122 | 7.37E-02 |
| PM08 | F01 | Val-Ser | dipeptide (N-source) | 0.0455 | <0.122 | 6.23E-01 |
| PM6-8 | A1 | No PM substrate | Control | 0.0489 | 2.690 | 9.80E-02 |
| PM6-8 | All Wells | All PM substrates | Control | 0.0467 | 2.423 | 3.62E-02 |
| PM6-8 | All Wells | All PM substrates but no C. difficile | Control | 0.0423$^d$ | <0.122$^e$ | NA |

$^a$OD (750 nm) difference between C. difficile under certain PM substrate (condition) and the same substrate without C. difficile.
$^b$Toxin concentrations in the CHO-k1 assay medium with C. difficile supernatant collected from different PM conditions, which were calculated from the average dye reduction rate by the CHO-k1 cells according to the equations in Table 1.
$^c$The P values were obtained from t-test on the dye reduction rates of CHO-k1 cells in the presence or absence of C. difficile supernatants collected from different PM conditions.
$^d$Average OD (750 nm) value of all uninoculated PM substrates from PM1-8.
$^e$This value is a result of calculation based on dye reduction rate of CHO-k1 cells in the presence of PM substrates of PM1-8 without C. difficile inoculation. It is a measure of zero toxin.

Some PM substrates demonstrated an inhibition of C. difficile toxin production, or a complete elimination of toxin production. These data were <0.122 ng/ml in CHO-k1 assay medium, or correspondingly <2.562 ng/ml in bacterial supernatant, which were indistinguishable from no C. difficile control. See Table 5. These concentrations were so low that they were out of the reliable range of dye reduction measurement.

Figure 14:
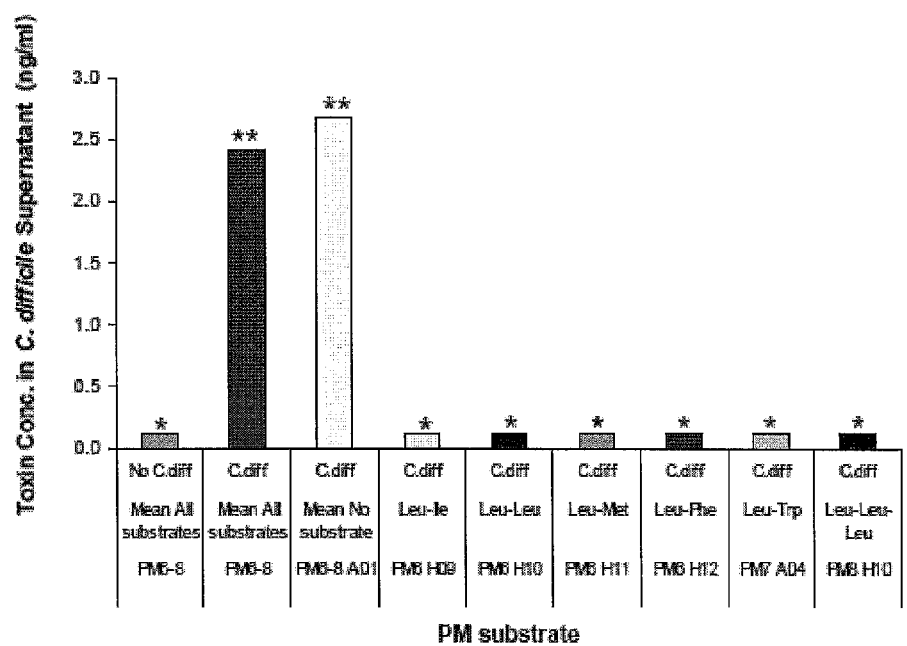
FIG. 14 presents exemplary data showing the repression of C. difficile toxin production by leucine dipeptides and the triple leucine tripeptide. * Since the dye reduction rate by CHO-k1 cells under the condition was greater than the upper limit indicated in Table 1, the estimated minimum toxin concentration value (0.12 ng/ml) measurable in this assay was taken for plotting purpose, which was actually <0.12 ng/ml or could even be 0 ng/ml. ** The corresponding dye reduction rates were within the range covered by the equation in Table 1. Therefore, these toxin concentrations were obtained from the rates by calculation. Because all C. difficile supernatants were diluted when tested in CHO-k1 cell assay medium, the actual toxin concentrations in the supernatants were all 21 fold higher than the displayed values.

Notable among the toxin production inhibitor group were several leucine dipeptides (leu-leu, leu-ile, leu-met, leu-phe, and leu-trp, and the leu-leu-leu tripeptide. Given the average toxin production of 57 ng/ml in the bacterial supernatant (or 2.690 ng/ml in the cell assay medium) from the no PM substrate control and 51 ng/ml (or 2.423 ng/ml in the cell assay medium) from all PM substrate controls of PM 6 through 8, and also given that the bacterial mass under those conditions were all comparable, the substrates that gave very low or no toxin production may in fact repress toxin production by C. difficile. See, FIG. 14 and Table 5.

The data presented herein demonstrate that with the type strain of C. difficile, ATCC 9689, toxin B production was strongly inhibited by some dipeptides containing leucine and the triple-leucine tripeptide as nitrogen sources in the presence of glucose. This appears to be consistent with previous observations of leucine's enhancement of down-regulation via CodY. For example, leucine peptides may be taken up more efficiently than leucine. Although it is not necessary to understand the mechanism of the invention, it is believed that leucine peptides are broadly and rapidly active in suppressing toxin production, and can be utilized to prevent and/or inhibit C. difficile induced toxicity in patients. CodY, a global regulator of gene expression, directly binds to the promoter of tcdR with high affinity, down-regulating toxin genes tcdA and tcdB. This binding is enhanced by GTP and branched-chain amino acids (i.e., for example, leucine, isoleucine, and valine). Therefore, CodY may integrate toxin production with the nutrient status of C. difficile. Underwood et al., "Characterization of the sporulation initiation pathway of Clostridium difficile and its role in toxin production" J Bacteriol 191: 7296-7305 (2009); Saujet et al., "The key sigma factor of transition phase, SigH, controls sporulation, metabolism, and virulence factor expression in Clostridium difficile" J Bacteriol 193: 3186-3196 (2011); Dineen et al., "Repression of Clostridium difficile toxin gene expression by CodY" Mol Microbiol 66: 206-219 (2007); and Dineen et al., "Integration of metabolism and virulence by Clostridium difficile CodY" J Bacteriol 192: 5350-5362 (2010).

Figure 15:
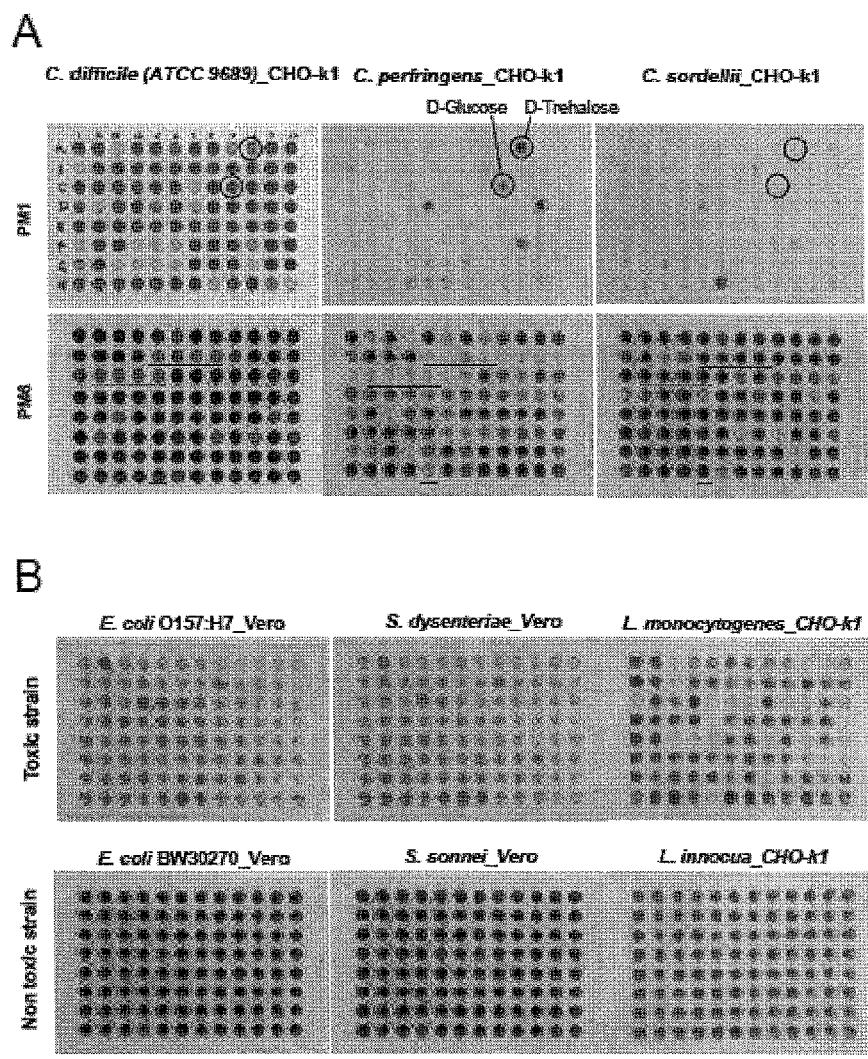
FIG. 15 presents exemplary data showing the cell-based cytotoxicity assay of other bacteria. Darker colors indicate higher dye reduction rate and less toxin produced in that well; lighter color indicates lower dye reduction rate and more toxin produced in that well.

Additional experiments were performed to demonstrate the general applicability of this assay technology to diverse toxin producing bacteria. Using CHO-k1 or Vero cells we could demonstrate variable toxicity from the PM panel supernatants of C. perfringens, C. tetani, C. sordellii, Bacillus cereus, Escherichia coli O157 (Vero), Shigella dysenteriae (Vero), and Listeria monocytogenes. See FIG. 15. Preliminary data, however, shows that protamine did not inactivate crude toxin preparations from bacteria including, but not limited to, E. coli O157, B. cerus, C. perfringens and C. sordellii, or when tested with purified Shiga toxin 1 and Shiga toxin 2.

IX. Therapeutic Implications

Reliable, quantitative, and robust assays for functional toxins are useful in scientific research and clinical practice. For example, a quantitative, colorimetric assays using the tetrazolium salt MTT to measure mammalian cell proliferation and cytotoxicity were previously reported. Mosmann T., "Rapid colorimetric assay for cellular growth and survival: application to proliferation and cytotoxicity assays" J Immunol Methods 65: 55-63 (1983). Since then, colorimetric assays have been applied in numerous research studies. In addition to its applications in anti-cancer drug research and other toxicity studies, colorimetric assays have been used with bacterial cytotoxin studies including measurement of cytotoxcity of C. difficile toxin. Chung et al., "The (3-(4,5-dimethylthiazol-2-yl)-2,5-diphenyltetrazolium) colorimetric assay for the quantitation of Actinobacillus pleuropneumoniae cytotoxin" Can J Vet Res 57: 159-165 (1993); Yang et al., "Expression of recombinant Clostridium difficile toxin A and B in Bacillus megaterium" BMC Microbiol 8: 192

(2008); Mahida et al., "Effect of *Clostridium difficile* toxin A on human intestinal epithelial cells: induction of interleukin 8 production and apoptosis after cell detachment" *Gut* 38: 337-347 (1996); Mullan et al., "Primary human colonic myofibroblasts are resistant to *Clostridium difficile* toxin A-induced, but not toxin B-induced, cell death" *Infect Immun* 79: 1623-1630 (2011); and Rothman S. W., "Technique for measuring 50% end points in cytotoxicity assays for *Clostridium difficile* toxins" *J Clin Pathol* 39: 672-676 (1986).

The application of colorimetric dyes significantly reduces the labor time because quantitation of color change avoids the laborious and subjective counting of rounded cells. However, the above described prior colorimetric assays have significant disadvantages in that they require solubilization of dye and reading of the plates manually with a microplate reader. This compromises the efficiency of the assays and does not allow one to collect high throughput kinetic data for analysis.

Through quantitative analysis, the data presented herein show that CPE is inversely correlated with dye reduction rate of the cells: the stronger the CPE, the lower the dye reduction rate. Furthermore, both toxin-induced CPE and decreased dye reduction rate were specifically and simultaneously prevented by the anti-toxin antibodies. The close correlation between the predicted toxin concentrations calculated from the regression equations and the prepared concentrations (Table 1) indicates that the equations obtained using the standard toxin are reliable and accurate over a wide range (>3 logs) of toxin concentration. Thus, the basis of determining the levels of *C. difficile* toxin production under various culture conditions can be accurately established.

It has been estimated that toxin B of *C. difficile* is 1000 times more potent than toxin A. Preliminary data also show that the indicator cell lines (CHO-k1 and Vero) were much more sensitive to toxin B than to toxin A (data not shown). Because of these large differences, trace or equivalent amounts of toxin A contamination in toxin B preparations would be of no consequence in the cell rounding assay, and therefore identifies a significant disadvantage of the cell rounding assay. IgY anti-toxin B polyclonal antibodies were capable of completely protecting the cells from purified standard toxin B. See FIG. 10. As expected, the anti-toxin B IgY almost completely protected the cells from the crude toxin preparations collected from 96-well PM panels as well. See, FIGS. 12A-D.

As a cell-based cytotoxicity assay, embodiments of the presently disclosed invention have gold standard reliability and makes the traditional cytotoxicity assay objectively quantifiable, more efficient, shorter in turn-around time (1 day rather than 2 or 3 days), and amenable to high throughput testing. More importantly, by eliminating subjective scoring of cell rounding, it allows results from different laboratories to be compared.

Combining this toxin assay method with various PM culture conditions (in 96-well plates) provides another unique advantage over the traditional methods used in toxin research. It allows scientists to simultaneously study hundreds to thousands of culture conditions that may positively or negatively affect toxin production by *C. difficile* or other toxigenic microorganisms. Using this approach, toxin production by *C. difficile* ATCC 9689 was measured under very diverse nutritional conditions, including 768 carbon, nitrogen, phosphorus, sulfur, and other nutrient sources (data not shown). Measuring hundreds of culture conditions in a quantitative and high throughput manner provides a broad perspective on toxin regulation and thus increases the probability of meaningful discoveries in toxin research. It provides another dimension beyond the effects of genetic changes.

X. Pharmaceutical Formulations

The present invention further provides pharmaceutical compositions (e.g., comprising the compounds described above). The invention should not be limited by the method of formulation or the method of delivery. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, an enema, or suppository administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

EXPERIMENTAL

Example I

Microwell Dye Reduction Metabolic Assay

This example describes a method to determine cell viability by measuring the reduction in a dye measuring energy substrate utilization. CHO-k1 cell cultures were placed in a standard microwell array (e.g., for example a 12×8 array). Approximately, 20,000 cells/ml were placed in each well containing 50 microliters of an RPMI 1640 assay medium comprising 2 mM glucose, 2 mM glutamine, 2% fetal bovine serum and 0.9% phosphate buffered saline. After twenty-four hours the cells were washed with fresh medium and an aliquot of a commercially available metabolic substrate utilization dye indicator was added (e.g., for example, Biolog Dye Mix MB).

The assay was initiated by adding *Clostridium difficile* Toxin B and an inhibitor protein/peptide (e.g. for example, protamine) such that a dose response curve of the inhibitor protein/peptide could be determined at various *C. difficile* Toxin B concentrations. One example of a microwell array set-up is as follows:

|  |  | 1 | 2 | 32 | 4 | 5 | 6 | 7 | 8 | 9 | 10 | 11 | 12 |
|---|---|---|---|---|---|---|---|---|---|---|---|---|---|
| ToxB (ng/ml) | A | 800 | 400 | 200 | 100.00 | 50.00 | 25.00 | 12.50 | 6.25 | 3.13 | 1.56 | 0.78 | 0.00 |
| ToxB (ng/ml) | B | 800 | 400 | 200 | 100.00 | 50.00 | 25.00 | 12.50 | 6.25 | 3.13 | 1.56 | 0.78 | 0.00 |
| ToxB (ng/ml) | C | 800 | 400 | 200 | 100.00 | 50.00 | 25.00 | 12.50 | 6.25 | 3.13 | 1.56 | 0.78 | 0.00 |
| ToxB (ng/ml) | D | 800 | 400 | 200 | 100.00 | 50.00 | 25.00 | 12.50 | 6.25 | 3.13 | 1.56 | 0.78 | 0.00 |
| ToxB (ng/ml) | E | 800 | 400 | 200 | 100.00 | 50.00 | 25.00 | 12.50 | 6.25 | 3.13 | 1.56 | 0.78 | 0.00 |
| ToxB (ng/ml) | F | 800 | 400 | 200 | 100.00 | 50.00 | 25.00 | 12.50 | 6.25 | 3.13 | 1.56 | 0.78 | 0.00 |
| ToxB (ng/ml) | G | 800 | 400 | 200 | 100.00 | 50.00 | 25.00 | 12.50 | 6.25 | 3.13 | 1.56 | 0.78 | 0.00 |
| ToxB (ng/ml) | H | 800 | 400 | 200 | 100.00 | 50.00 | 25.00 | 12.50 | 6.25 | 3.13 | 1.56 | 0.78 | 0.00 |

|  |  | 1 | 2 | 32 | 4 | 5 | 6 | 7 | 3 | 9 | 10 | 11 | 12 |
|---|---|---|---|---|---|---|---|---|---|---|---|---|---|
| Protamine sulfate (ug/ml) | A | 100.0 | 100.0 | 100.0 | 100.0 | 100.0 | 100.0 | 100.0 | 100.0 | 100.0 | 100.0 | 100.0 | 0.0 |
| Protamine sulfate (ug/ml) | B | 50.0 | 50.0 | 50.0 | 50.0 | 50.0 | 50.0 | 50.0 | 50.0 | 50.0 | 50.0 | 50.0 | 0.0 |
| Protamine sulfate (ug/ml) | C | 25.0 | 25.0 | 25.0 | 25.0 | 25.0 | 25.0 | 25.0 | 25.0 | 25.0 | 25.0 | 25.0 | 0.0 |
| Protamine sulfate (ug/ml) | D | 12.5 | 12.5 | 12.5 | 12.5 | 12.5 | 12.5 | 12.5 | 12.5 | 12.5 | 12.5 | 12.5 | 0.0 |
| Protamine sulfate (ug/ml) | E | 6.3 | 6.3 | 6.3 | 6.3 | 6.3 | 6.3 | 6.3 | 6.3 | 6.3 | 6.3 | 6.3 | 0.0 |
| Protamine sulfate (ug/ml) | F | 3.1 | 3.1 | 3.1 | 3.1 | 3.1 | 3.1 | 3.1 | 3.1 | 3.1 | 3.1 | 3.1 | 0.0 |
| Protamine sulfate (ug/ml) | G | 1.6 | 1.6 | 1.6 | 1.6 | 1.6 | 1.6 | 1.6 | 1.6 | 1.6 | 1.6 | 1.6 | 0.0 |
| Protamine sulfate (ug/ml) | H | 0.8 | 0.8 | 0.8 | 0.8 | 0.8 | 0.8 | 0.8 | 0.8 | 0.8 | 0.8 | 0.8 | 0.0 |

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. The dosing can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 μg to 100 g per kg of body weight, once or more daily.

Figure 2:
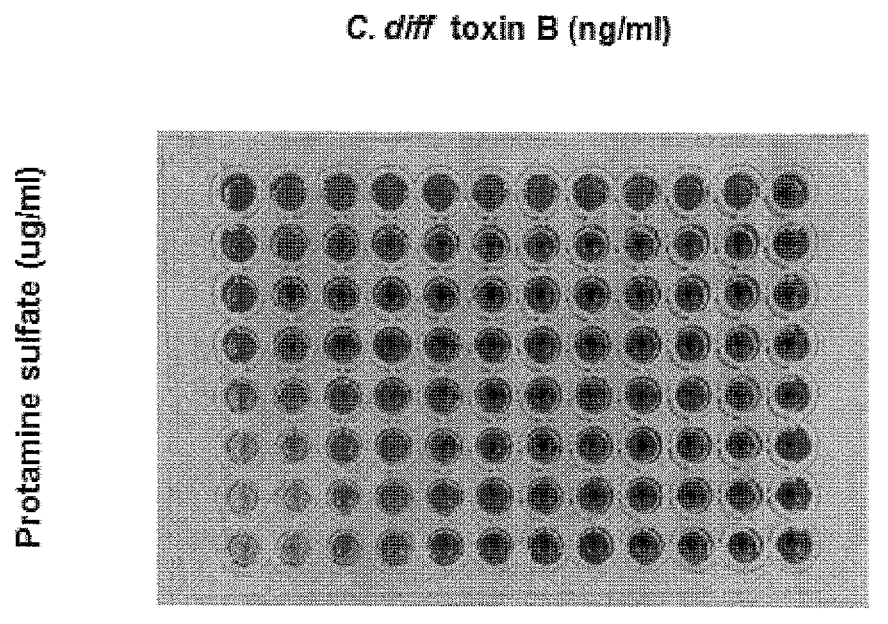

The results of this set-up shows dye color reductions from right-to-left across each row that corresponds with increased *C. difficile* Toxin B concentration in the same protamine concentration. See FIG. 2. Color dye reduction reflect glucose utilization in the tested cells, such that the lighter colored wells indicate cells with low glucose utilization. Low glucose utilization is an indicator of cell viability. Consequently, the ability of inhibitor proteins/peptides disclosed herein can be tested for bacterial toxin inactivation efficacy.

Example II

Protamine Inactivation of *C. difficile* Toxin B

CHO-k1 cell culture were used in this cytotoxicity assay in accordance with Example I. *C. difficile* toxin B at concentrations of 100 ng/ml, 33.3 ng/ml, 11.1 ng/ml, 3.7 ng/ml and 1.2 ng/ml were added to the cell culture followed immediately by protamine sulfate in 3-fold dilutions.

The cells were then incubated in $CO_2$ incubator at 37° C. for 20 hrs. Biolog Dye Mix MB was added to the cells at the end of the $CO_2$ incubation, which is immediately followed by incubation in Biolog OmniLog instrument at 36° C. for 3 hrs. The dye reduction occurred during the 3 hrs and the signals of dye reduction (color is darker when more dye molecules are reduced by the cells) were recorded automatically by the instrument.

The healthier the cells are, the higher the dye reduction rate is. Based on regression analysis on the dye reduction rates under various concentrations of the standard toxin B alone (the toxin standard curve), the reduced toxin levels under various concentration of protamine sulfate were observed and quantified. See FIG. 3. All measured toxin concentrations are plotted against the actual toxin concentration. X-axis: actual (prepared) toxin B; Y-axis: measured toxin B by dye reduction rate. Both axes are in arithmetic scale.

Note that the curve of standard toxin B sits almost at 45 degree angle, validating the reliability of the regression analysis. Note that at all tested concentrations of protamine sulfate can dramatically reduce the toxin B at high level.

Example III

Protamine III-2 Peptide Inactivation of *C. difficile* Toxin B

CHO-k1 cell culture were used in this cytotoxicity assay in accordance with Example I. *C. difficile* toxin B at concentrations of 100 ng/ml, 33.3 ng/ml, 11.1 ng/ml, 3.7 ng/ml and 1.2 ng/ml were added to the cell culture followed immediately by protamine III-2 peptide in 3-fold dilutions.

The cells were then incubated in $CO_2$ incubator at 37° C. for 20 hrs. Biolog Dye Mix MB was added to the cells at the end of the $CO_2$ incubation, which is immediately followed by incubation in Biolog OmniLog instrument at 36° C. for 3 hrs. The dye reduction occurred during the 3 hrs and the signals of dye reduction (color is darker when more dye molecules are reduced by the cells) were recorded automatically by the instrument.

The healthier the cells are, the higher the dye reduction rate is. Based on regression analysis on the dye reduction rates under various concentrations of the standard toxin B alone (the toxin standard curve), the reduced toxin levels under various concentration of protamine sulfate were observed and quantified. See FIG. 5. All measured toxin concentrations are plotted against the actual toxin concentration. X-axis: actual (prepared) toxin B; Y-axis: measured toxin B by dye reduction rate. Both axes are in arithmetic scale.

Note that the curve of standard toxin B sits almost at 45 degree angle, validating the reliability of the regression analysis. Note that at all tested concentrations of protamine sulfate can dramatically reduce the toxin B at high level.

Example IV

Polyarginine Inactivation of *C. difficile* Toxin B

CHO-k1 cell culture were used in this cytotoxicity assay in accordance with Example I. *C. difficile* toxin B at concentrations of 100 ng/ml, 33.3 ng/ml, 11.1 ng/ml, 3.7 ng/ml and 1.2 ng/ml were added to the cell culture followed immediately by polyarginine in 3-fold dilutions.

The cells were then incubated in CO2 incubator at 37° C. for 20 hrs. Biolog Dye Mix MB was added to the cells at the end of the CO2 incubation, which is immediately followed by incubation in Biolog OmniLog instrument at 36° C. for 3 hrs. The dye reduction occurred during the 3 hrs and the signals of dye reduction (color is darker when more dye molecules are reduced by the cells) were recorded automatically by the instrument. The healthier the cells are, the higher the dye reduction rate is. Based on regression analysis on the dye reduction rates under various concentrations of the standard toxin B alone (the toxin standard curve), the reduced toxin levels under various concentration of polyarginine were observed and quantified. See FIG. 7. All measured toxin concentrations are plotted against the actual toxin concentration. X-axis: actual (prepared) toxin B; Y-axis: measured toxin B by dye reduction rate. Both axes are in arithmetic scale.

Note that the curve of standard toxin B sits almost at 45 degree angle, validating the reliability of the regression analysis. Note that at all tested concentrations of polyarginine can dramatically reduce the toxin B at high level.

Example V

A Screening Method to Identify Modulators of Microbial Toxin Production

Phenotype MicroArray (PM) panels, chemicals, toxins, anti-toxins, bacterial strains, and mammalian cells lines. PM panels, inoculating fluid IF-0a GN/GP Base (or IF-0a for short), Redox Dye Mix MB and inoculating fluid IF-M1 are from Biolog, Inc. (Hayward, Calif., USA). Other chemicals were purchased from Sigma-Aldrich (St. Louis, Mo., USA) unless specified otherwise. Yeast extract (YE) was from Oxoid (UK). *Clostridium difficile* toxin A and toxin B were from List Biological Laboratory (Listlab, Campbell, Calif., USA). Anti-toxin A and anti-toxin B polyclonal chicken IgYs from Gallus Immunotech (Fergus, Ontario, Canada). *Clostridium difficile* strains: type strain ATCC 9689 and Toxinotype 0 strain VPI 10463 (ATCC 43255) were purchased from American Type Culture Collection (ATCC, Manassas, Va., USA). Some other bacteria obtained through commercial sources include: *C. perfringens* (ATCC 25763), *C. tetani* (ATCC 19406), *C. sordellii* (ATCC 9714), *Bacillus cereus* (ATCC 14579), *Escherichia coli* O157:H7 (ATCC 43894), *Shigella dysenteriae* (ATCC 11835), *S. sonnei* (ATCC 25931), *L. innocua* (ATCC 33090). Others were obtained as gifts, including *E. coli* BW30270 (from Barry Wanner, USA), *Listeria monocytogenes* strains P14 and P14-A (from Jose Vasquez-Boland, UK). Mammalian cell lines CHO-k1, Vero, HT-29, and A549 were also purchased from ATCC. Cell growth medium RPMI 1640, fetal bovine serum (FBS), Penicillin-Streptomycin, glutamine, and trypsin were purchased from Invitrogen. Glucose solution and RPMI 1640 vitamins stock solution were from Sigma-Aldrich. For preparation of bacterial culture supernatants we used 96-well filter plates (Pall, 0.2 uM pore size, PN 8015). For cell-based cytotoxicity assay and subsequent cellular dye reduction assay we used tissue culture treated 96-well plates (BD Falcon 353072).

A work flow diagram depicts and summarizes the testing and assay for measuring *C. difficile* toxin production under different culture conditions in a 96-well panel format. See, FIG. 16. This process is applied to all anaerobic bacteria. The incubation time for different bacteria may vary before toxins are collected. To collect toxins from aerobic bacteria, the process is the same as that for anaerobic bacteria except aerobic bacteria are incubated in an aerobic incubator instead of an anaerobic chamber.

Bacterial Preculture and Inoculum Preparation.

*C. difficile* and other anaerobic bacterial strains were routinely pre-cultured on BUA+B agar (Biolog) inside an anaerobic chamber (Bactron IV) at 36° C. with a gas atmosphere of 5% H2, 5% CO2, and 90% N2. *C. difficile* fresh cultures (20-24 h) on BUA+B were used for PM panel inoculation. The inoculum of *C. difficile* was from fresh cultures in late log phase that were examined and found to be free of endospores. Inocula were conveniently prepared by removing colonies from a BUA+B agar plate using a swab, and resuspending in IF-0a inoculating fluid. The bacterial suspension was adjusted in IF-0a to achieve a 40% transmittance (T40) using a Biolog Turbidimeter, which was measured spectrophotometrically as 0.139+0.002 O.D. (at 750 nm in a Multiskan Ascent). The suspension was further diluted 1:16 in IF-0a. This cell density was directly used for PM panel inoculation. This inoculum (T40 1:16) when plated on BUA+B gave a count of 9.07E+07 CFUs/ml.

PM Panel Special Pretreatment for Anaerobic Bacteria.

Prior to their use with anaerobic bacteria, all PM panels were converted to an anaerobic state by thorough deoxygenation. To do this, the PM panel packaging bags are cut to open one end. Two oxygen absorbers (Ageless sachets, Mitsubishi) are inserted into the bag along with the original desiccate sachet and then the bag is resealed with a heat sealer. If the bag has a good seal, the sachets will absorb the air in the bag so that the packaging appears as if it is shrink-wrapped. This operation can be done on the lab bench. The resealed PM panels can be kept at room temperature for 1 day and then stored in the refrigerator (2-8° C.) for additional days or months before use. The thoroughly deoxygenated panels can then be warmed up to room temperature before being used in an experiment. The panels are resealed well, which allows the Ageless sachets to completely remove oxygen from the panels. It is not recommended to deoxygenate the PM panels by putting them in the anaerobic chamber because the moisture inside the chamber may destabilize some substrates. To deoxygenate Biolog IF-0a GN/GP Base, the bottle caps were loosened and the bottles were placed inside the anaerobic chamber for 3 days before use.

PM Media and Bacterial Toxin Collection.

PM panels are 96-well microplates containing a different substrate in each well. PM1 and PM2 are carbon source panels. PM3, 6, 7, and 8 are nitrogen source panels. PM4 contains various phosphate and sulfur sources; PM5 contains various biosynthesis pathway endproducts and nutrient supplements. In addition to a unique substrate, each well of these metabolic panels also contains the needed minimal medium components but without ferric chloride, tetrazolium violet, and sodium pyruvate added.

To produce and collect bacterial culture supernatants containing toxins, *C. difficile* or other bacterial species were inoculated in duplicate or triplicate into panels PM1-8 at T40 1:16 and incubated for an optimum length of time, e.g., 3 days for *C. difficile*. The inoculating fluid for *C. difficile* consists of Biolog IF-0a GN/GP Base, 0.5× RPMI 1640 vitamins, and 0.2% yeast extract (sterilized by filtration) for PM1, 2 or 0.05% yeast extract for PM3, 4, 5, 6, 7, and 8. To provide the carbon source in PM3-8, glucose at a final concentration of 5 mM was added to the inoculating fluid. To obtain a crude toxin preparation free of cells, the bacterial liquid cultures were transferred to a 96-well filter plate (Pall) and filtered by centrifugation at 2000 rpm for 5 minutes (Hermle Z 360 K, rotor model C-0360-50). The filtrates were used immediately (the same day) or kept in a sterile 96-well plate (Biolog) sealed with tape for brief storage at 4° C. before use. No bacteria controls (i.e. no toxin controls, or PM substrate controls) were PM substrate solutions rehydrated from the corresponding PM panels, obtained by following the same procedure for bacterial supernatants described above except no bacteria inoculated into the PM panels. All experiments described above were done multiple times (2-4) as independent replicates (2-3) and each was followed by cytotoxicity assays on the bacterial filtrates collected. All aerobic bacteria tested in this study were handled on the bench and grown on Biolog agar medium (BUG+B) as a preculture and then inoculated and incubated aerobically in PM panels without shaking. After 24 h of incubation in the panels at 37° C., the bacterial supernatants were collected using the 96-well filter plates and centrifugation, and then handled and tested as described above.

The toxin-containing supernatants should be used as soon as possible after harvest because refrigeration temperature does not completely maintain the toxins during long term storage and the potency of the toxins was observed to decrease over time. Better long term storage of the toxins requires purification and lyophilization. These same procedures were followed for preparing PM substrate suspension controls without *C. difficile*.

Determination of Bacterial Mass in Wells of PM Panels.

To determine bacterial mass kinetics, PM panels inoculated with *C. difficile* in triplicate were removed from the anaerobic chamber at 24, 48, or 72 h of incubation. Bacterial mass was determined by measuring the optical density of wells at 750 nm using a microplate reader (Multiskan Ascent). Compared to 48 h or 72 h, the values of OD-750 at 24 h of incubation were the highest under most PM well conditions. With a few exceptions, all the OD-750 values decreased more or less at 48 h and further decreased at 72 h. Given the nutritional limitations of the media, the growth was limited, but the kinetic trends were clear and similar to each other among the various culture conditions.

To determine the bacterial mass at the end point and before harvesting toxin-containing supernatants, the PM panels with *C. difficile* in replicates were removed from the anaerobic chamber at 72 h and the mass was determined as described above. To obtain net bacterial mass, the OD-750 value from the corresponding well of an uninoculated plate is subtracted from the OD-750 value of the inoculated well. These bacterial net mass values can be used to normalize toxin production when a specific cell productivity measurement is needed.

Mammalian Cell Lines and their Cytotoxicity and Neutralization Assays.

Cell lines CHO-k1, Vero, HT-29, and A549 were grown at 37° C. in an incubator atmosphere of 5% CO2 in standard T75 cell culture flasks with RPMI 1640 medium plus 10% FBS and 1× Pen/Strep, without phenol red. The cells were allowed to grow for 20-24 h before harvesting for experiments. This young cell culture was then prepared in an assay medium (Biolog IF-M1 inoculating fluid plus 2 mM glucose, 2 mM glutamine, 2% FBS, and 1× Pen/Strep) at a density of 200,000 cells per ml. A 100 µl aliquot of this cell suspension was plated into each well of tissue culture treated 96-well microplates, the assay plate. Five microliters of toxin preparation either from serial titrations of purified standard toxin (Listlab) or from supernatants of microbial culture filtrates collected from each PM culture condition were transferred to each well of the assay plate immediately following the cell plating. This makes the toxin preparation a 21-fold dilution [(5+100)/5]. Five µl of corresponding PM substrate solution were used as no toxin control. The assay plates of the treated indicator cells were then incubated at 37° C. with 5% CO2 for 18-20 h.

For neutralization experiments, a neutralizing antibody was mixed with the indicator cell suspension immediately prior to cell plating. The cell plating was followed immediately by addition of the toxin preparation to the plated cells. After 18-20 h of incubation, cell morphologies were observed under the microscope (10×10 magnification) and images were recorded with a digital camera. These same cells were further tested for their ability to reduce the Biolog Dye Mix MB. Twenty µl of the dye solution was transferred to each well. The plates were then placed into the OmniLog PM instrument (Biolog, Inc.) for incubation and kinetic data collection for 3 h or longer. As the dye is reduced, a purple color is irreversibly developed. The healthier the cells are, the more NADH they produce and the higher the rate of dye reduction.

Determination of Dye Reduction Rate by the Mammalian Cells.

The dye reduction by indicator cells was kinetically measured during the incubation period by the OmniLog instrument. The resulting dye reduction values were imported into a PM analysis program, which can calculate a rate of dye reduction based on a linear regression algorithm. The rate of dye reduction within the first few hours of incubation (e.g., 0 through 3 h) was calculated. The effects of standard *C. difficile* toxin B or *C. difficile* supernatants collected from different PM conditions on the rate were studied. The average rates of the standard toxin or of the supernatants were used in all subsequent calculations.

To correct for the influence (positive or negative) of a given PM substrate on the rate, the dye reduction rate of the PM substrate control is measured. A ratio of a PM substrate is derived from the control set and defined as a quotient of the average rate of all wells for a given PM panel and its replicas (e.g., an average of 3 PM1 panels is obtained from 3×96 wells) divided by the average of a given well in that panel. So, if a PM substrate has a positive influence on the dye reduction rate of the indicator cell line, the ratio will be smaller than 1, otherwise greater than 1. For example, D-glucose (e.g., PM1 C9) could positively influence dye reduction because the substrate control experiments showed it was associated with higher dye reduction rate than the panel average (78.48 vs 74.93). So, the ratio for D-glucose is smaller than 1 (0.9547). The average dye reduction rate of CHO-k1 in the presence of *C. difficile* supernatant from D-glucose is 57.19, but the corrected dye reduction rate is 57.19×0.9547=54.6.

In general, the rate of dye reduction by cells can be affected by many factors, e.g., cell lines, cell number and fitness, adverse environmental conditions (e.g., toxic chemicals), nutrient or energy source used to support cell respiration, the type of redox dyes, and so on. In these experiments, however, all factors and conditions given are controlled except the levels of toxins produced by the microorganism under the different culture conditions in the PM panels.

As mentioned above, all experiments were done multiple times and as independent replicates. From these, the averages and standard deviations of dye reduction rates were calculated, which are expressed as a mean+/−standard deviation and plotted as histograms exemplified by FIG. 3D. Statistical analyses were performed using Microsoft Office Excel TTEST via Excel automation on the rates between the experimental set and the control set on a well-by-well basis. The data were treated as two-tailed distributions with unequal variance. The difference is considered significant only if the probability of no difference between the means of the two sets is smaller than 5%, P<0.05.

Determination of Toxin Production by *C. difficile* and Other *Clostridium* Species.

Anaerobic bacteria used in this study including *C. difficile, C. perfringens, C. tetani*, and *C. sordellii*, were incubated for three days before removal from the anaerobic chamber for cell mass measurement and toxin collection: (1) Establishment of standard curves of toxin and dye reduction rate. *C. difficile* toxins A and B from Listlab were used as standards to determine the relationship between toxin concentration and the corresponding level of inhibition of dye reduction rate by the indicator mammalian cells. Cytotoxicity and dye reduction assays with serial 2-fold or 3-fold standard toxin titrations were performed multiple times. For a given indicator cell line, the known concentrations of the toxin (ng/ml) used in the assay were plotted on the Y-axis with a log 10 scale against corresponding dye reduction rates plotted on the X-axis. Using Microsoft Office Excel 2002 software, the plots were fitted to curves by non-linear regression analyses and the equations for predicting concentrations from the rates were generated; (2) Determination of toxin production by *C. difficile* under different PM culture conditions. The corrected average dye reduction rates from the *C. difficile* supernatants were used to calculate the toxin concentration according to the equations. The calculations were performed robustly by employing Excel worksheet functions.

Example VI

In Vivo Rescue of Systemic Bacterial Infections by Toxin Inactivation

Two groups of animals (e.g., mice) will be injected with an infectious dose of *C. difficile*. When the groups of animals exhibit symptoms of bacterial infection, one group will be administered a protamine III-2 peptide intravenously and the other group will be administered a vehicle control. In some experiments, the animals will be pre-treated with an antibiotic after administration of *C. difficile* but before the administration of protamine III-2.

It is expected that the animals in the vehicle control group will continue to exhibit symptoms of bacterial infection that will become more severe over time. In contrast, the group administered the protamine III-2 peptide will recover.

Example VII

In Vivo Rescue of Systemic Bacterial Infections by Reduced Toxin Production

Two groups of animals (e.g., mice) will be injected with an infectious dose of *C. difficile*. When the groups of animals exhibit symptoms of bacterial infection, one group will be administered a leucine dipeptide or leucine tripeptide intravenously and the other group will be administered a vehicle control. In some experiments, the animals will be pre-treated with an antibiotic after administration of *C. difficile* but before the administration of protamine III-2.

It is expected that the animals in the vehicle control group will continue to exhibit symptoms of bacterial infection that will become more severe over time. In contrast, the group administered the leucine dipeptide or leucin tripeptide will recover.

We claim:

1. A method, comprising:
 a) providing;
  i) a patient comprising a Clostridia toxin;
  ii) a therapeutic cationic polypeptide selected from the group consisting of protamine, a protamine fragment comprising a plurality of arginine amino acid clusters, protamine III-2, polyarginine and polylysine;
 b) administering said therapeutic polypeptide to said patient; and
 c) inactivating said bacterial toxin with said cationic polypeptide.

2. The method of claim 1, wherein said bacterial toxin is systemic.

3. The method of claim 1, wherein said bacterial toxin is localized to the colon.

4. The method of claim 1, wherein said Clostridia toxin is selected from the group consisting of a *C. difficile* Toxin B and a *C. difficile* Toxin A.

5. The method of claim 1, wherein said inactivating comprises a specific binding between said bacterial toxin and said cationic protein.

6. The method of claim 1, wherein said inactivating comprising a non-specific binding between said bacterial toxin and said cationic protein.

7. The method of claim 1, wherein said administering is selected from at least one group consisting of parenterally and/or via enema or suppository.

8. The method of claim 1, wherein said method further comprises administering an antibiotic before step (b).

9. The method of claim 1, wherein said method further comprises administering a toxin production inhibitor before step (b).

10. The method of claim 1, wherein said cationic polypeptide is formulated into a pharmaceutical composition.

* * * * *

SEQUENCE LISTING

<160> NUMBER OF SEQ ID NOS: 22

<210> SEQ ID NO 1
<211> LENGTH: 32
<212> TYPE: PRT
<213> ORGANISM: Artificial Sequence
<220> FEATURE:
<223> OTHER INFORMATION: Synthetic

<400> SEQUENCE: 1

Pro Arg Arg Arg Arg Ser Ser Ser Arg Pro Ile Arg Arg Arg Pro
1               5                   10                  15

Arg Arg Ala Ser Arg Arg Arg Arg Arg Gly Gly Arg Arg Arg Arg
            20                  25                  30

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Arg Arg Arg Arg Pro Arg Arg Ala Ser
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Pro Arg Arg Arg Arg Ser Ser Ser Arg Pro Ile
1               5                   10

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Pro Arg Arg Arg Arg Ser Ser Ser Arg Pro Ile Arg Arg Arg Pro
1               5                   10                  15

Arg Arg Ala Ser Arg Arg
            20

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Arg Arg Arg Arg Arg Arg Gly Gly Arg Arg Arg Arg
1               5                   10

<210> SEQ ID NO 6
<211> LENGTH: 20
<212> TYPE: PRT
<213> ORGANISM: Artificial Sequence
<220> FEATURE:

```
<223> OTHER INFORMATION: Synthetic

<400> SEQUENCE: 6

Arg Pro Ile Arg Arg Arg Pro Arg Ala Ser Arg Arg Arg
1               5                   10                  15

Arg Arg Gly Gly
            20

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Pro Arg Arg Arg Arg Ser Ser Ser Arg Pro
1               5                   10

<210> SEQ ID NO 8
<211> LENGTH: 32
<212> TYPE: PRT
<213> ORGANISM: Artificial Sequence
<220> FEATURE:
<223> OTHER INFORMATION: Synthetic

<400> SEQUENCE: 8

Pro Arg Arg Arg Arg Ser Ser Ser Arg Pro Val Arg Arg Arg Pro
1               5                   10                  15

Arg Arg Val Ser Arg Arg Arg Arg Arg Gly Gly Arg Arg Arg
            20                  25                  30

<210> SEQ ID NO 9
<211> LENGTH: 18
<212> TYPE: PRT
<213> ORGANISM: Artificial Sequence
<220> FEATURE:
<223> OTHER INFORMATION: Synthetic

<400> SEQUENCE: 9

Val Arg Arg Arg Arg Pro Arg Arg Val Ser Arg Arg Arg Arg Arg
1               5                   10                  15

Gly Gly

<210> SEQ ID NO 10
<211> LENGTH: 21
<212> TYPE: PRT
<213> ORGANISM: Artificial Sequence
<220> FEATURE:
<223> OTHER INFORMATION: Synthetic

<400> SEQUENCE: 10

Arg Arg Arg Arg Pro Arg Arg Val Ser Arg Arg Arg Arg Arg Gly
1               5                   10                  15

Gly Arg Arg Arg Arg
            20

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11
```

```
Arg Arg Arg Arg Arg Arg Gly Gly Arg Arg Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

Arg Arg Arg Arg Ser Ser Ser Arg Pro Val Arg Arg Arg Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Pro Arg Arg Arg Arg Ser Ser Ser Arg Pro
1               5                   10

<210> SEQ ID NO 14
<211> LENGTH: 32
<212> TYPE: PRT
<213> ORGANISM: Artificial Sequence
<220> FEATURE:
<223> OTHER INFORMATION: Synthetic

<400> SEQUENCE: 14

Pro Arg Arg Arg Arg Ser Ser Arg Arg Pro Val Arg Arg Arg Pro
1               5                   10                  15

Arg Arg Val Ser Arg Arg Arg Arg Arg Gly Gly Arg Arg Arg
            20                  25                  30

<210> SEQ ID NO 15
<211> LENGTH: 18
<212> TYPE: PRT
<213> ORGANISM: Artificial Sequence
<220> FEATURE:
<223> OTHER INFORMATION: Synthetic

<400> SEQUENCE: 15

Val Arg Arg Arg Pro Arg Arg Val Ser Arg Arg Arg Arg Arg
1               5                   10                  15

Gly Gly

<210> SEQ ID NO 16
<211> LENGTH: 21
<212> TYPE: PRT
<213> ORGANISM: Artificial Sequence
<220> FEATURE:
<223> OTHER INFORMATION: Synthetic

<400> SEQUENCE: 16

Arg Arg Arg Arg Pro Arg Val Ser Arg Arg Arg Arg Arg Gly
1               5                   10                  15

Gly Arg Arg Arg Arg
            20

<210> SEQ ID NO 17
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 17

Arg Arg Arg Arg Arg Arg Gly Gly Arg Arg Arg Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Arg Arg Arg Arg Arg Arg Gly Gly Arg Arg Arg Arg
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Arg Arg Arg Arg Pro Arg Arg Val
1               5

<210> SEQ ID NO 20
<211> LENGTH: 30
<212> TYPE: PRT
<213> ORGANISM: Artificial Sequence
<220> FEATURE:
<223> OTHER INFORMATION: Synthetic

<400> SEQUENCE: 20

Pro Arg Arg Arg Arg Ala Ser Arg Arg Ile Arg Arg Arg Arg Arg Pro
1               5                   10                  15

Arg Val Ser Arg Arg Arg Arg Arg Gly Gly Arg Arg Arg Arg
            20                  25                  30

<210> SEQ ID NO 21
<211> LENGTH: 18
<212> TYPE: PRT
<213> ORGANISM: Artificial Sequence
<220> FEATURE:
<223> OTHER INFORMATION: Synthetic

<400> SEQUENCE: 21

Pro Arg Arg Arg Arg Ala Ser Arg Arg Ile Arg Arg Arg Arg Arg Pro
1               5                   10                  15

Arg Val

<210> SEQ ID NO 22
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 22

Ile Arg Arg Arg Arg Arg Pro Arg
1               5
```